(12) United States Patent
Woloszko et al.

(10) Patent No.: US 8,012,153 B2
(45) Date of Patent: Sep. 6, 2011

(54) ROTARY ELECTROSURGICAL APPARATUS AND METHODS THEREOF

(75) Inventors: Jean Woloszko, Mountain View, CA (US); Robert H. Dahla, Sunnyvale, CA (US)

(73) Assignee: ArthroCare Corporation, Austin, TX (US)

( * ) Notice: Subject to any disclaimer, the term of this patent is extended or adjusted under 35 U.S.C. 154(b) by 1050 days.

(21) Appl. No.: 10/565,116

(22) PCT Filed: Jul. 16, 2004

(86) PCT No.: PCT/US2004/022803
§ 371 (c)(1),
(2), (4) Date: Jan. 17, 2006

(87) PCT Pub. No.: WO2005/009213
PCT Pub. Date: Feb. 3, 2005

(65) Prior Publication Data
US 2006/0178670 A1    Aug. 10, 2006

Related U.S. Application Data

(60) Provisional application No. 60/488,134, filed on Jul. 16, 2003.

(51) Int. Cl.
*A61B 18/14* (2006.01)
(52) U.S. Cl. .......................................... 606/48; 606/50
(58) Field of Classification Search ............... 606/32–50
See application file for complete search history.

(56) References Cited

U.S. PATENT DOCUMENTS

| | | | |
|---|---|---|---|
| 2,050,904 A | 4/1936 | Trice | 219/31 |
| 2,056,377 A | 10/1939 | Wappler | 125/303 |
| 2,275,167 A | 3/1942 | Bierman | 606/50 |
| 3,633,425 A | 1/1972 | Sanford | 73/356 |
| 3,699,967 A | 10/1972 | Anderson | 606/37 |
| 3,707,149 A | 12/1972 | Hao et al. | 128/303.14 |
| 3,812,858 A | 5/1974 | Oringer | 604/22 |
| 3,815,604 A | 6/1974 | O'Malley et al. | 128/305 |
| 3,828,780 A | 8/1974 | Morrison, Jr. | 128/275 |
| 3,901,242 A | 8/1975 | Storz | 128/303 |
| 3,920,021 A | 11/1975 | Hiltebrandt | 128/303 |

(Continued)

FOREIGN PATENT DOCUMENTS

DE    2521719    11/1976

(Continued)

OTHER PUBLICATIONS

Buchelt, et al. "Excimer Laser Ablation of Fibrocartilage: An in Vitro and in Vivo Study", Lasers in Surgery and Medicine, vol. 11, pp. 271-279, 1991.

(Continued)

*Primary Examiner* — Michael Peffley
*Assistant Examiner* — Ronald Hupczey, Jr.
(74) *Attorney, Agent, or Firm* — Matthew Scheele; Brian Szymczak

(57) ABSTRACT

Electrosurgical systems, apparatus, and methods for the controlled removal and treatment of a target tissue. An instrument of the invention includes a rotating member housed longitudinally within a shaft, a tissue removal port disposed at the shaft distal end portion, and an active electrode disposed at the instrument distal end. The active electrode is adapted to electrosurgically remove at least a portion of the target tissue as the rotating member rotates within the shaft. According to alternative embodiments, the active electrode may be disposed on the rotating member or on the shaft.

37 Claims, 11 Drawing Sheets

U.S. PATENT DOCUMENTS

| | | | |
|---|---|---|---|
| 3,939,839 A | 2/1976 | Curtiss | 128/303 |
| 3,945,375 A * | 3/1976 | Banko | 600/104 |
| 3,964,487 A | 6/1976 | Judson | 606/39 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,203,444 A * | 5/1980 | Bonnell et al. | 604/22 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 600/505 |
| 4,248,231 A | 2/1981 | Herczog et al. | 128/303 |
| 4,269,174 A | 5/1981 | Adair | 128/842 |
| 4,274,414 A | 6/1981 | Johnson et al. | 606/170 |
| 4,326,529 A | 4/1982 | Doss et al. | 128/303 |
| 4,381,007 A | 4/1983 | Doss | 128/303 |
| 4,411,266 A | 10/1983 | Cosman | 606/49 |
| 4,418,692 A | 12/1983 | Guay | 606/42 |
| 4,429,694 A | 2/1984 | McGreevy | 128/303.14 |
| 4,474,179 A | 10/1984 | Koch | 606/40 |
| 4,476,862 A | 10/1984 | Pao | 128/303 |
| 4,483,338 A | 11/1984 | Bloom et al. | 606/50 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,572,206 A | 2/1986 | Geddes et al. | 600/505 |
| 4,580,557 A | 4/1986 | Hertzmann | 606/12 |
| 4,582,057 A | 4/1986 | Auth et al. | 606/31 |
| 4,587,975 A | 5/1986 | Salo et al. | 600/506 |
| 4,590,934 A | 5/1986 | Malis et al. | 128/303 |
| 4,593,691 A | 6/1986 | Lindstrom et al. | 128/303 |
| 4,641,649 A | 2/1987 | Walinsky et al. | 606/33 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,736,743 A | 4/1988 | Daikuzono | 128/303.1 |
| 4,737,678 A | 4/1988 | Hasegawa | 313/36 |
| 4,762,128 A | 8/1988 | Rosenbluth | 128/343 |
| 4,765,331 A | 8/1988 | Petruzzi et al. | 128/303 |
| 4,785,806 A | 11/1988 | Deckelbaum | 128/303.1 |
| 4,785,823 A | 11/1988 | Eggers et al. | 128/692 |
| 4,805,616 A | 2/1989 | Pao | 128/303 |
| 4,813,429 A | 3/1989 | Eshel et al. | 128/736 |
| 4,815,462 A | 3/1989 | Clark | 606/170 |
| 4,823,791 A | 4/1989 | D'Amelio et al. | 123/303 |
| 4,827,911 A | 5/1989 | Broadwin et al. | 604/22 |
| 4,832,048 A | 5/1989 | Cohen | 128/786 |
| 4,860,752 A | 8/1989 | Turner | 607/102 |
| 4,903,696 A | 2/1990 | Stasz et al. | 606/37 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,940,064 A | 7/1990 | Desai | 607/122 |
| 4,943,290 A | 7/1990 | Rexroth et al. | 606/45 |
| 4,955,377 A | 9/1990 | Lennox et al. | 607/105 |
| 4,966,597 A | 10/1990 | Cosman | 606/50 |
| 4,967,765 A | 11/1990 | Turner et al. | 128/785 |
| 4,968,314 A | 11/1990 | Michaels | 606/7 |
| 4,976,709 A | 12/1990 | Sand | 606/5 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,437 A | 4/1991 | Sterzer | 428/786 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,037,421 A | 8/1991 | Boutacoff et al. | 606/15 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,057,743 A | 10/1991 | Krasko et al. | 313/639 |
| 5,061,266 A | 10/1991 | Hakky | 606/15 |
| 5,078,717 A | 1/1992 | Parins et al. | 606/48 |
| 5,080,660 A | 1/1992 | Buelna | 606/45 |
| 5,083,565 A | 1/1992 | Parins | 600/374 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,092,339 A | 3/1992 | Geddes et al. | 606/505 |
| 5,093,877 A | 3/1992 | Aita et al. | 385/34 |
| 5,098,431 A | 3/1992 | Rydell | 606/48 |
| 5,099,840 A | 3/1992 | Goble et al. | 128/422 |
| 5,102,410 A | 4/1992 | Dressel | 606/15 |
| 5,103,804 A | 4/1992 | Abele et al. | 600/116 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,137,530 A | 8/1992 | Sand | 606/5 |
| 5,147,354 A | 9/1992 | Boutacoff et al. | 606/15 |
| 5,151,098 A | 9/1992 | Loertscher | 606/16 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,176,528 A | 1/1993 | Fry et al. | 439/181 |
| 5,178,620 A | 1/1993 | Eggers et al. | 606/41 |
| 5,183,338 A | 2/1993 | Wickersheim et al. | 374/131 |
| 5,190,517 A | 3/1993 | Zieve et al. | 604/22 |
| 5,191,883 A | 3/1993 | Lennox et al. | 607/102 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,455 A | 6/1993 | Tan | 606/9 |
| 5,217,457 A | 6/1993 | Delahuerga et al. | 606/42 |
| 5,217,459 A | 6/1993 | Kamerling | 606/48 |
| 5,230,334 A | 7/1993 | Klopotek | 601/3 |
| 5,234,428 A | 8/1993 | Kaufman | 606/45 |
| 5,246,438 A | 9/1993 | Langberg | 606/33 |
| 5,249,585 A | 10/1993 | Turner et al. | 607/99 |
| 5,255,980 A | 10/1993 | Thomas et al. | 374/161 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,269,794 A * | 12/1993 | Rexroth | 606/180 |
| 5,273,524 A | 12/1993 | Fox et al. | 604/21 |
| 5,277,201 A | 1/1994 | Stern | 607/98 |
| 5,277,696 A | 1/1994 | Hagen | 606/49 |
| 5,279,299 A | 1/1994 | Imran | 600/393 |
| 5,281,216 A | 1/1994 | Klicek | 606/42 |
| 5,281,218 A | 1/1994 | Imran | 606/41 |
| 5,282,797 A | 2/1994 | Chess | 606/9 |
| 5,282,799 A | 2/1994 | Rydell | 606/48 |
| 5,290,273 A | 3/1994 | Tan | 606/9 |
| 5,290,282 A | 3/1994 | Casscells | 606/29 |
| 5,293,868 A | 3/1994 | Nardella | 600/373 |
| 5,300,069 A | 4/1994 | Hunsberger et al. | 606/37 |
| 5,300,099 A | 4/1994 | Rudie | 607/101 |
| 5,301,687 A | 4/1994 | Wong et al. | 607/116 |
| 5,304,169 A | 4/1994 | Sand | 606/5 |
| 5,304,170 A | 4/1994 | Green | 606/9 |
| 5,306,238 A | 4/1994 | Fleenor | 606/42 |
| 5,312,395 A | 5/1994 | Tan et al. | 606/9 |
| 5,312,400 A | 5/1994 | Bales et al. | 606/41 |
| 5,314,406 A | 5/1994 | Arias et al. | 604/21 |
| 5,318,563 E | 6/1994 | Malis et al. | 606/38 |
| 5,322,507 A | 6/1994 | Costello et al. | 128/4 |
| 5,324,254 A | 6/1994 | Phillips | 604/21 |
| 5,330,470 A | 7/1994 | Hagen | 606/42 |
| 5,330,518 A | 7/1994 | Neilson et al. | 607/101 |
| 5,334,140 A | 8/1994 | Phillips | 604/35 |
| 5,334,183 A | 8/1994 | Wuchinich | 606/46 |

| Patent No. | Date | Inventor | Class |
|---|---|---|---|
| 5,334,193 A | 8/1994 | Nardella | 606/41 |
| 5,335,668 A | 8/1994 | Nardella | 600/547 |
| 5,336,217 A | 8/1994 | Buys et al. | 606/9 |
| 5,336,220 A | 8/1994 | Ryan et al. | 604/22 |
| 5,336,443 A | 8/1994 | Odashima | 252/511 |
| 5,342,357 A | 8/1994 | Nardella | 606/40 |
| 5,348,554 A | 9/1994 | Imran et al. | 606/41 |
| 5,364,395 A | 11/1994 | West, Jr. | 606/46 |
| 5,366,443 A | 11/1994 | Eggers et al. | 252/511 |
| 5,370,642 A | 12/1994 | Keller | 606/9 |
| 5,370,644 A | 12/1994 | Langberg | 606/33 |
| 5,370,675 A | 12/1994 | Edwards et al. | 607/101 |
| 5,374,261 A | 12/1994 | Yoon | 604/385.01 |
| 5,374,265 A | 12/1994 | Sand | 606/5 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,395,363 A | 3/1995 | Billings et al. | 606/41 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,405,376 A | 4/1995 | Mulier et al. | 607/127 |
| 5,417,687 A | 5/1995 | Nardella et al. | 606/32 |
| 5,419,767 A | 5/1995 | Eggers et al. | 604/114 |
| 5,423,803 A | 6/1995 | Tankovich | 606/9 |
| 5,423,810 A | 6/1995 | Goble et al. | 606/40 |
| 5,423,844 A * | 6/1995 | Miller | 606/171 |
| 5,423,882 A | 6/1995 | Jackman et al. | 607/122 |
| 5,431,649 A | 7/1995 | Mulier et al. | 606/41 |
| 5,433,708 A | 7/1995 | Nichols et al. | 604/113 |
| 5,436,566 A | 7/1995 | Thompson et al. | 324/713 |
| 5,437,662 A | 8/1995 | Nardella | 606/40 |
| 5,437,664 A | 8/1995 | Cohen et al. | 606/42 |
| 5,438,302 A | 8/1995 | Goble | 331/167 |
| 5,441,499 A | 8/1995 | Fritzsch | 606/45 |
| 5,445,634 A | 8/1995 | Keller | 606/9 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,458,597 A | 10/1995 | Edwards et al. | 606/41 |
| 5,462,545 A | 10/1995 | Wang et al. | 606/41 |
| 5,472,443 A | 12/1995 | Cordis et al. | 606/48 |
| 5,484,435 A | 1/1996 | Fleenor et al. | 606/46 |
| 5,487,385 A | 1/1996 | Avitall | 600/374 |
| 5,490,850 A | 2/1996 | Ellman et al. | 606/45 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,730 A | 4/1996 | Edwards et al. | 606/41 |
| 5,514,130 A | 5/1996 | Baker | 606/41 |
| 5,520,685 A | 5/1996 | Wojciechowicz | 606/49 |
| 5,536,267 A | 7/1996 | Edwards et al. | 606/41 |
| 5,542,915 A | 8/1996 | Edwards et al. | 604/22 |
| 5,542,928 A | 8/1996 | Evans et al. | 604/113 |
| 5,545,161 A | 8/1996 | Imran | 606/41 |
| 5,554,152 A | 9/1996 | Aita | 606/7 |
| 5,556,397 A | 9/1996 | Long et al. | 606/48 |
| 5,562,720 A | 10/1996 | Desai | 606/210 |
| 5,567,890 A | 10/1996 | Lindberg et al. | 75/243 |
| 5,569,242 A | 10/1996 | Lax et al. | 606/42 |
| 5,571,100 A | 11/1996 | Goble et al. | 606/41 |
| 5,579,764 A | 12/1996 | Goldreyer | 600/374 |
| 5,584,872 A | 12/1996 | LaFontaine et al. | 607/117 |
| 5,599,350 A | 2/1997 | Schulze et al. | 606/51 |
| 5,607,421 A | 3/1997 | Jeevanandam et al. | 606/15 |
| 5,609,151 A | 3/1997 | Mulier et al. | 128/642 |
| 5,609,573 A | 3/1997 | Sandock | 604/22 |
| 5,618,293 A | 4/1997 | Sample et al. | 606/170 |
| 5,626,576 A | 5/1997 | Janssen | 606/41 |
| 5,633,578 A | 5/1997 | Eggers et al. | 323/301 |
| 5,643,255 A | 7/1997 | Organ | 606/41 |
| 5,647,869 A | 7/1997 | Goble et al. | 606/37 |
| 5,658,278 A | 8/1997 | Imran et al. | 606/41 |
| 5,660,567 A | 8/1997 | Nierlich et al. | 439/620.21 |
| 5,660,836 A | 8/1997 | Knowlton | 607/101 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,681,308 A | 10/1997 | Edwards et al. | 606/41 |
| 5,683,366 A | 11/1997 | Eggers et al. | 604/114 |
| 5,688,267 A | 11/1997 | Panescu et al. | 606/41 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,713,896 A | 2/1998 | Nardella | 606/50 |
| 5,715,817 A | 2/1998 | Steven-Wright et al. | 600/373 |
| 5,722,975 A | 3/1998 | Edwards et al. | 606/41 |
| 5,725,524 A | 3/1998 | Mulier et al. | 606/41 |
| 5,743,870 A | 4/1998 | Edwards | 604/22 |
| 5,743,903 A | 4/1998 | Stern et al. | 606/31 |
| 5,746,746 A | 5/1998 | Garito et al. | 606/41 |
| 5,749,869 A | 5/1998 | Lindenmeier et al. | 606/34 |
| 5,755,753 A | 5/1998 | Knowlton | 607/98 |
| 5,766,153 A | 6/1998 | Eggers et al. | 604/114 |
| 5,769,843 A | 6/1998 | Abela et al. | 606/10 |
| 5,769,847 A | 6/1998 | Panescu et al. | 606/42 |
| 5,782,795 A * | 7/1998 | Bays | 604/22 |
| 5,785,705 A | 7/1998 | Baker | 606/32 |
| 5,786,578 A | 7/1998 | Christy et al. | 219/720 |
| 5,800,429 A | 9/1998 | Edwards | 606/41 |
| 5,800,431 A | 9/1998 | Brown | 606/42 |
| 5,807,384 A | 9/1998 | Mueller | 606/7 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,843,019 A | 12/1998 | Eggers et al. | 604/22 |
| 5,843,078 A | 12/1998 | Sharkey | 606/41 |
| 5,843,106 A | 12/1998 | Heisler | 606/167 |
| 5,855,277 A | 1/1999 | Apps et al. | 606/35 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,871,524 A | 2/1999 | Knowlton | 607/101 |
| 5,873,855 A | 2/1999 | Eggers et al. | 604/114 |
| 5,873,877 A | 2/1999 | McGaffigan | 606/41 |
| 5,876,398 A | 3/1999 | Mulier et al. | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,893,848 A | 4/1999 | Negus et al. | 606/41 |
| 5,895,386 A | 4/1999 | Odell et al. | 606/50 |
| 5,897,553 A | 4/1999 | Mulier | 606/41 |
| 5,902,272 A | 5/1999 | Eggers et al. | 604/114 |
| 5,904,681 A * | 5/1999 | West, Jr. | 606/41 |
| 5,906,613 A | 5/1999 | Mulier et al. | 606/41 |
| 5,919,219 A | 7/1999 | Knowlton | 607/102 |
| 5,941,876 A | 8/1999 | Nardella et al. | 606/45 |
| 5,944,715 A | 8/1999 | Goble et al. | 606/41 |
| 5,954,716 A | 9/1999 | Sharkey et al. | 606/32 |
| 5,964,754 A | 10/1999 | Osypka | 606/37 |
| 5,964,786 A | 10/1999 | Ochs et al. | 607/5 |
| 5,976,127 A | 11/1999 | Lax | 606/32 |
| 5,980,516 A | 11/1999 | Mulier et al. | 606/41 |
| 5,980,545 A | 11/1999 | Pacala et al. | 606/170 |
| 5,984,919 A | 11/1999 | Hilal et al. | 606/45 |
| 6,004,319 A | 12/1999 | Goble et al. | 606/48 |
| 6,007,533 A * | 12/1999 | Casscells et al. | 606/45 |
| 6,013,076 A | 1/2000 | Goble et al. | 606/41 |
| 6,015,406 A | 1/2000 | Goble et al. | 606/41 |
| 6,016,809 A | 1/2000 | Mulier et al. | 128/898 |
| 6,024,733 A | 2/2000 | Eggers et al. | 604/500 |
| 6,027,501 A | 2/2000 | Goble et al. | 606/41 |
| 6,030,383 A | 2/2000 | Benderev | 606/45 |
| 6,032,673 A * | 3/2000 | Savage et al. | 128/898 |
| 6,032,674 A | 3/2000 | Eggers et al. | 606/41 |
| 6,036,681 A | 3/2000 | Hooven | 604/506 |
| 6,039,734 A | 3/2000 | Goble et al. | 606/41 |
| 6,045,532 A | 4/2000 | Eggers et al. | 604/114 |

| Patent No. | Kind | Date | Inventor(s) | Class |
|---|---|---|---|---|
| 6,047,700 | A | 4/2000 | Eggers et al. | 128/898 |
| 6,053,172 | A | 4/2000 | Hovda et al. | 128/898 |
| 6,056,746 | A | 5/2000 | Goble et al. | 606/48 |
| 6,063,079 | A | 5/2000 | Hovda et al. | 606/41 |
| 6,063,081 | A | 5/2000 | Mulier et al. | 606/45 |
| 6,066,134 | A | 5/2000 | Eggers et al. | 606/32 |
| 6,068,628 | A | 5/2000 | Fanton et al. | 606/41 |
| 6,074,386 | A | 6/2000 | Goble et al. | 606/34 |
| 6,086,583 | A | 7/2000 | Ouchi | 606/41 |
| 6,090,106 | A | 7/2000 | Goble et al. | 606/41 |
| 6,091,995 | A | 7/2000 | Ingle et al. | 607/138 |
| 6,093,186 | A | 7/2000 | Goble | 606/34 |
| 6,096,037 | A | 8/2000 | Mulier et al. | 606/49 |
| 6,102,046 | A | 8/2000 | Weinstein et al. | 128/898 |
| 6,105,581 | A | 8/2000 | Eggers et al. | 128/898 |
| 6,109,268 | A | 8/2000 | Thapliyal et al. | 128/898 |
| 6,110,169 | A | 8/2000 | Mueller et al. | 606/48 |
| 6,117,109 | A | 9/2000 | Eggers et al. | 604/114 |
| 6,126,682 | A | 10/2000 | Sharkey et al. | 607/96 |
| 6,142,992 | A | 11/2000 | Cheng et al. | 606/34 |
| 6,149,620 | A | 11/2000 | Baker et al. | 604/22 |
| 6,152,923 | A | 11/2000 | Ryan | 606/51 |
| 6,156,031 | A | 12/2000 | Aita et al. | 606/33 |
| 6,159,194 | A | 12/2000 | Eggers et al. | 604/500 |
| 6,159,208 | A | 12/2000 | Hovda et al. | 606/41 |
| 6,162,217 | A | 12/2000 | Kannenberg et al. | 606/34 |
| 6,168,593 | B1 | 1/2001 | Sharkey et al. | 606/34 |
| 6,174,309 | B1 | 1/2001 | Wrublewski et al. | 606/45 |
| 6,179,824 | B1 | 1/2001 | Eggers et al. | 604/500 |
| 6,179,836 | B1 | 1/2001 | Eggers et al. | 606/45 |
| 6,183,469 | B1 | 2/2001 | Thapliyal et al. | 606/41 |
| 6,190,381 | B1 | 2/2001 | Olsen et al. | 606/32 |
| 6,193,715 | B1 | 2/2001 | Wrublewski et al. | 606/45 |
| 6,197,021 | B1 | 3/2001 | Panescu et al. | 606/31 |
| 6,203,542 | B1 | 3/2001 | Ellsberry et al. | 606/41 |
| 6,210,402 | B1 | 4/2001 | Olsen et al. | 606/32 |
| 6,210,405 | B1 | 4/2001 | Goble et al. | 606/41 |
| 6,214,001 | B1 | 4/2001 | Casscells et al. | 606/41 |
| 6,217,575 | B1 | 4/2001 | DeVore et al. | 606/41 |
| 6,224,592 | B1 | 5/2001 | Eggers et al. | 606/32 |
| 6,228,078 | B1 | 5/2001 | Eggers | 606/32 |
| 6,228,081 | B1 | 5/2001 | Goble | 606/34 |
| 6,234,178 | B1 | 5/2001 | Goble et al. | 606/32 |
| 6,235,020 | B1 | 5/2001 | Cheng et al. | 606/34 |
| 6,237,604 | B1 | 5/2001 | Burnside et al. | 128/897 |
| 6,238,391 | B1 | 5/2001 | Olsen et al. | 606/41 |
| 6,238,393 | B1 | 5/2001 | Mulier et al. | 607/127 |
| 6,254,600 | B1 | 7/2001 | Willink et al. | 606/41 |
| 6,261,286 | B1 | 7/2001 | Goble et al. | 606/34 |
| 6,261,311 | B1 | 7/2001 | Sharkey et al. | 607/96 |
| 6,264,650 | B1 | 7/2001 | Hovda | 606/32 |
| 6,264,652 | B1 | 7/2001 | Eggers et al. | 606/41 |
| 6,267,757 | B1 | 7/2001 | Aita et al. | 606/33 |
| 6,270,460 | B1 | 8/2001 | McCartan et al. | 600/459 |
| 6,277,112 | B1 | 8/2001 | Underwood et al. | 606/32 |
| 6,280,441 | B1 | 8/2001 | Ryan | 606/45 |
| 6,283,961 | B1 | 9/2001 | Underwood et al. | 604/41 |
| 6,293,942 | B1 | 9/2001 | Goble et al. | 606/38 |
| 6,296,636 | B1 | 10/2001 | Cheng et al. | 606/32 |
| 6,296,638 | B1 | 10/2001 | Davison et al. | 606/41 |
| 6,302,903 | B1 | 10/2001 | Mulier et al. | 607/105 |
| 6,306,134 | B1 | 10/2001 | Goble et al. | 606/42 |
| 6,308,089 | B1 | 10/2001 | von der Rur et al. | 600/338 |
| 6,309,387 | B1 | 10/2001 | Eggers et al. | 606/41 |
| 6,312,408 | B1 | 11/2001 | Eggers et al. | 604/114 |
| 6,312,429 | B1 | 11/2001 | Burbank et al. | 606/47 |
| 6,315,774 | B1 | 11/2001 | Daniel et al. | 606/15 |
| 6,322,494 | B1 | 11/2001 | Bullivant et al. | 600/104 |
| 6,322,549 | B1 | 11/2001 | Eggers et al. | 604/500 |
| 6,325,799 | B1 | 12/2001 | Goble | 606/41 |
| 6,327,505 | B1 | 12/2001 | Medhkour et al. | 607/99 |
| 6,328,736 | B1 | 12/2001 | Mulier et al. | 606/45 |
| 6,336,926 | B1 | 1/2002 | Goble | 606/34 |
| 6,346,107 | B1 | 2/2002 | Cucin | 606/49 |
| 6,355,006 | B1 | 3/2002 | Ryaby et al. | 601/2 |
| 6,355,032 | B1 | 3/2002 | Hovda et al. | 606/32 |
| 6,358,248 | B1 | 3/2002 | Mulier et al. | 606/41 |
| 6,363,937 | B1 | 4/2002 | Hovda et al. | 128/898 |
| 6,364,877 | B1 | 4/2002 | Goble et al. | 606/34 |
| 6,379,350 | B1 | 4/2002 | Sharkey et al. | 606/41 |
| 6,379,351 | B1 | 4/2002 | Thapliyal et al. | 606/41 |
| 6,391,025 | B1 | 5/2002 | Weinstein et al. | 606/41 |
| 6,391,028 | B1 | 5/2002 | Fanton et al. | 606/45 |
| 6,398,781 | B1 | 6/2002 | Goble et al. | 606/41 |
| 6,409,722 | B1 | 6/2002 | Hoey et al. | 606/34 |
| 6,409,724 | B1 | 6/2002 | Penny et al. | 606/41 |
| 6,416,507 | B1 | 7/2002 | Eggers et al. | 606/32 |
| 6,416,508 | B1 | 7/2002 | Eggers et al. | 606/32 |
| 6,416,509 | B1 | 7/2002 | Goble et al. | 606/37 |
| 6,428,539 | B1 | 8/2002 | Baxter et al. | 606/49 |
| 6,432,103 | B1 | 8/2002 | Ellsberry et al. | 606/41 |
| 6,432,105 | B1 | 8/2002 | Ellman et al. | 606/48 |
| 6,440,129 | B1 | 8/2002 | Simpson | 606/42 |
| 6,468,274 | B1 | 10/2002 | Alleyne et al. | 606/32 |
| 6,468,275 | B1 | 10/2002 | Wampler et al. | 606/48 |
| 6,482,201 | B1 | 11/2002 | Olsen et al. | 606/41 |
| 6,482,202 | B1 | 11/2002 | Goble et al. | 606/32 |
| 6,491,690 | B1 | 12/2002 | Goble et al. | 606/41 |
| 6,510,854 | B2 | 1/2003 | Goble | 128/898 |
| 6,514,250 | B1 | 2/2003 | Jahns et al. | 606/41 |
| 6,517,498 | B1 | 2/2003 | Burbank et al. | 600/564 |
| 6,517,535 | B2 | 2/2003 | Edwards | 606/41 |
| 6,530,922 | B2 | 3/2003 | Cosman | 606/34 |
| 6,540,741 | B1 | 4/2003 | Underwood et al. | 606/32 |
| 6,557,559 | B1 | 5/2003 | Eggers et al. | 128/898 |
| 6,558,382 | B2 | 5/2003 | Jahns et al. | 606/41 |
| 6,575,968 | B1 | 6/2003 | Eggers et al. | 606/41 |
| 6,575,969 | B1 | 6/2003 | Rittman, III et al. | 606/41 |
| 6,578,579 | B2 | 6/2003 | Burnside | 128/897 |
| 6,582,423 | B1 | 6/2003 | Thapliyal et al. | 606/32 |
| 6,589,237 | B2 | 7/2003 | Woloszko et al. | 606/41 |
| 6,595,990 | B1 | 7/2003 | Weinstein et al. | 606/41 |
| 6,597,950 | B2 | 7/2003 | Linder et al. | 607/8 |
| 6,602,248 | B1 | 8/2003 | Sharps et al. | 606/32 |
| 6,620,156 | B1 | 9/2003 | Garito et al. | 606/50 |
| 6,632,193 | B1 | 10/2003 | Davison et al. | 604/22 |
| 6,632,220 | B1 | 10/2003 | Eggers et al. | 606/41 |
| 6,632,230 | B2 | 10/2003 | Barry | 606/159 |
| 6,663,628 | B2* | 12/2003 | Peters | 606/45 |
| 6,699,206 | B2 | 3/2004 | Burbank et al. | 606/567 |
| 6,702,810 | B2 | 3/2004 | McClurken et al. | 606/34 |
| 6,746,447 | B2 | 6/2004 | Davison et al. | 606/41 |
| 6,749,604 | B1 | 6/2004 | Eggers et al. | 606/41 |
| 6,749,608 | B2 | 6/2004 | Garito et al. | 606/45 |
| 6,763,836 | B2 | 7/2004 | Tasto et al. | 128/898 |
| 6,770,071 | B2 | 8/2004 | Woloszko et al. | 606/41 |
| 6,780,178 | B2 | 8/2004 | Palanker et al. | 600/41 |
| 6,780,180 | B1 | 8/2004 | Goble et al. | 606/41 |
| 6,802,842 | B2 | 10/2004 | Ellman et al. | 606/45 |
| 6,805,130 | B2 | 10/2004 | Tasto et al. | 606/32 |
| 6,827,725 | B2 | 12/2004 | Batchelor et al. | 606/170 |
| 6,832,996 | B2 | 12/2004 | Woloszko et al. | 606/41 |
| 6,837,887 | B2 | 1/2005 | Woloszko et al. | 606/41 |
| 6,837,888 | B2 | 1/2005 | Ciarrocca et al. | 606/41 |
| 6,855,143 | B2 | 2/2005 | Davison et al. | 606/41 |
| 6,866,671 | B2 | 3/2005 | Tierney et al. | 606/130 |
| 6,878,149 | B2 | 4/2005 | Gatto | 606/46 |
| 6,890,307 | B2 | 5/2005 | Kokate et al. | 600/549 |
| 6,892,086 | B2 | 5/2005 | Russell | 600/372 |
| 6,896,674 | B1 | 5/2005 | Woloszko et al. | 606/41 |
| 6,904,303 | B2 | 6/2005 | Phan et al. | 600/374 |
| 6,920,883 | B2 | 7/2005 | Bessette et al. | 128/898 |
| 6,929,640 | B1 | 8/2005 | Underwood et al. | 606/32 |
| 6,949,096 | B2 | 9/2005 | Davison et al. | 606/41 |
| 6,960,204 | B2 | 11/2005 | Eggers et al. | 606/32 |
| 6,974,453 | B2 | 12/2005 | Woloszko et al. | 606/41 |
| 6,979,332 | B2* | 12/2005 | Adams | 606/45 |
| 6,979,601 | B2 | 12/2005 | Marr et al. | 438/132 |
| 6,984,231 | B2 | 1/2006 | Goble et al. | 606/37 |
| 6,986,700 | B2 | 1/2006 | Agarwal | 451/6 |
| 6,991,631 | B2 | 1/2006 | Woloszko et al. | 606/41 |
| 7,004,941 | B2 | 2/2006 | Tvinnereim et al. | 606/41 |
| 7,041,102 | B2 | 5/2006 | Truckai et al. | 606/51 |
| 7,070,596 | B1 | 7/2006 | Woloszko et al. | 606/41 |
| 7,090,672 | B2 | 8/2006 | Underwood et al. | 606/41 |
| 7,094,215 | B2 | 8/2006 | Davison et al. | 604/22 |
| 7,104,986 | B2 | 9/2006 | Hovda et al. | 606/32 |
| 7,131,969 | B1 | 11/2006 | Hovda et al. | 606/45 |

| Patent Number | Date | Inventor | Class |
|---|---|---|---|
| 7,150,747 B1 * | 12/2006 | McDonald et al. | 606/45 |
| 7,169,143 B2 | 1/2007 | Eggers et al. | 606/32 |
| 7,179,255 B2 | 2/2007 | Lettice et al. | 606/32 |
| 7,184,811 B2 | 2/2007 | Phan et al. | 600/374 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,261,712 B2 | 8/2007 | Burbank et al. | 606/49 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,276,063 B2 | 10/2007 | Davison et al. | 606/45 |
| 7,278,994 B2 | 10/2007 | Goble | 606/41 |
| 7,297,143 B2 | 11/2007 | Woloszko et al. | 606/41 |
| 7,297,145 B2 | 11/2007 | Ormsby et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,488,295 B2 | 2/2009 | Burbank et al. | 606/167 |
| 7,819,863 B2 | 10/2010 | Eggers et al. | 606/32 |
| 2001/0025177 A1 * | 9/2001 | Woloszko et al. | 606/41 |
| 2002/0029036 A1 | 3/2002 | Goble et al. | 606/38 |
| 2002/0038122 A1 * | 3/2002 | Peters | 606/45 |
| 2002/0049438 A1 | 4/2002 | Sharkey et al. | 606/41 |
| 2002/0072739 A1 | 6/2002 | Lee et al. | 606/47 |
| 2003/0013986 A1 | 1/2003 | Saadat | 600/549 |
| 2003/0028189 A1 | 2/2003 | Woloszko et al. | 604/41 |
| 2003/0088245 A1 | 5/2003 | Woloszko et al. | 606/41 |
| 2003/0130655 A1 | 7/2003 | Woloszko et al. | 606/45 |
| 2003/0158545 A1 | 8/2003 | Hovda et al. | 606/32 |
| 2003/0163126 A1 * | 8/2003 | West, Jr. | 606/41 |
| 2003/0171743 A1 * | 9/2003 | Tasto et al. | 606/32 |
| 2003/0208194 A1 | 11/2003 | Hovda et al. | 606/41 |
| 2003/0208196 A1 | 11/2003 | Stone | 606/41 |
| 2003/0209958 A1 | 11/2003 | Hwang et al. | 606/41 |
| 2003/0212396 A1 | 11/2003 | Eggers et al. | 606/41 |
| 2003/0216725 A1 | 11/2003 | Woloszko et al. | 606/41 |
| 2003/0216732 A1 | 11/2003 | Truckai et al. | 606/49 |
| 2004/0049180 A1 | 3/2004 | Sharps et al. | 606/32 |
| 2004/0116922 A1 | 6/2004 | Hovda et al. | 606/41 |
| 2004/0127893 A1 | 7/2004 | Hovda | 606/41 |
| 2004/0230190 A1 | 11/2004 | Dahla et al. | 604/41 |
| 2005/0004634 A1 | 1/2005 | Ricart et al. | 606/41 |
| 2005/0010205 A1 | 1/2005 | Hovda et al. | 606/32 |
| 2005/0033278 A1 | 2/2005 | McClurken et al. | 606/34 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0234439 A1 | 10/2005 | Underwood | 606/32 |
| 2005/0251134 A1 | 11/2005 | Woloszko et al. | 606/32 |
| 2005/0261754 A1 | 11/2005 | Woloszko | 606/32 |
| 2005/0288665 A1 | 12/2005 | Woloszko | 606/41 |
| 2006/0036237 A1 | 2/2006 | Davison et al. | 606/41 |
| 2006/0095031 A1 | 5/2006 | Ormsby | 606/34 |
| 2006/0178670 A1 | 8/2006 | Woloszko et al. | 606/48 |
| 2006/0189971 A1 | 8/2006 | Tasto et al. | 606/32 |
| 2006/0253117 A1 | 11/2006 | Hovda et al. | 128/898 |
| 2006/0259025 A1 | 11/2006 | Dahla | 607/108 |
| 2007/0010808 A1 | 1/2007 | Dahla | 606/41 |
| 2007/0106288 A1 | 5/2007 | Woloszko et al. | 606/41 |
| 2007/0112348 A1 | 5/2007 | Eggers et al. | 606/41 |
| 2007/0129715 A1 | 6/2007 | Eggers et al. | 606/32 |
| 2007/0149966 A1 | 6/2007 | Dahla et al. | 606/41 |
| 2007/0161981 A1 | 7/2007 | Sanders et al. | 606/41 |
| 2007/0179497 A1 | 8/2007 | Eggers et al. | 606/41 |
| 2007/0208334 A1 | 9/2007 | Woloszko et al. | 606/41 |
| 2007/0208335 A1 | 9/2007 | Woloszko et al. | 606/41 |
| 2007/0213700 A1 | 9/2007 | Davison et al. | 606/32 |
| 2007/0282323 A1 | 12/2007 | Woloszko et al. | 606/41 |
| 2008/0021447 A1 | 1/2008 | Davison et al. | 606/41 |
| 2008/0167646 A1 | 7/2008 | Godara et al. | 606/41 |
| 2008/0234673 A1 | 9/2008 | Marion et al. | 606/45 |
| 2008/0300590 A1 | 12/2008 | Horne et al. | 606/35 |
| 2009/0069807 A1 | 3/2009 | Eggers et al. | 606/48 |
| 2010/0042095 A1 | 2/2010 | Bigley et al. | 606/41 |
| 2010/0152724 A1 | 6/2010 | Marion et al. | 606/41 |
| 2010/0204690 A1 | 8/2010 | Bigley et al. | 606/41 |

FOREIGN PATENT DOCUMENTS

| | | |
|---|---|---|
| DE | 3930451 A1 | 3/1991 |
| DE | 4425015 | 1/1996 |
| DE | 296 09 350 | 8/1996 |
| DE | 195 37 084 | 4/1997 |
| DE | 296 19 029 | 4/1997 |
| DE | 102009057921 A1 | 6/2010 |
| EP | 0 502 268 | 9/1992 |
| EP | 0 515 867 | 12/1992 |
| EP | 543123 | 5/1993 |
| EP | 0 597 463 | 5/1994 |
| EP | 774926 | 3/1995 |
| EP | 0 650 701 | 5/1995 |
| EP | 0703461 A2 | 3/1996 |
| EP | 0740926 A2 | 11/1996 |
| EP | 0 754 437 | 1/1997 |
| EP | 923907 | 6/1999 |
| EP | 0 694 290 | 11/2000 |
| EP | 1149564 | 10/2001 |
| FR | 2313949 | 1/1977 |
| GB | 2037167 | 7/1980 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| GB | 2331247 | 5/1999 |
| GB | 2379878 | 3/2003 |
| GB | 2408936 | 6/2005 |
| JP | 57-57802 | 4/1982 |
| JP | 57-117843 | 7/1982 |
| JP | 57-183850 | 11/1982 |
| JP | 63-40099 | 8/1988 |
| JP | 9-501328 | 2/1997 |
| WO | 90/03152 | 4/1990 |
| WO | 90/07303 | 7/1990 |
| WO | 91/13650 | 9/1991 |
| WO | 92/21278 | 12/1992 |
| WO | 93/13816 | 7/1993 |
| WO | 93/20747 | 10/1993 |
| WO | 94/03134 | 2/1994 |
| WO | 94/04220 | 3/1994 |
| WO | 94/08654 | 4/1994 |
| WO | 94/10924 | 5/1994 |
| WO | 94/14383 | 7/1994 |
| WO | 94/26228 | 11/1994 |
| WO | 95/05780 | 3/1995 |
| WO | 95/05781 | 3/1995 |
| WO | 95/05867 | 3/1995 |
| WO | 95/10326 | 4/1995 |
| WO | 95/30373 | 11/1995 |
| WO | 95/34259 | 12/1995 |
| WO | 96/00042 | 1/1996 |
| WO | 96/07360 | 3/1996 |
| WO | 96/34568 | 11/1996 |
| WO | 96/35469 | 11/1996 |
| WO | 96/39914 | 12/1996 |
| WO | 96/39962 | 12/1996 |
| WO | 96/39964 | 12/1996 |
| WO | 96/39965 | 12/1996 |
| WO | 96/39967 | 12/1996 |
| WO | 97/00646 | 1/1997 |
| WO | 97/00647 | 1/1997 |
| WO | 97/15238 | 5/1997 |
| WO | 97/18765 | 5/1997 |
| WO | 97/18768 | 5/1997 |
| WO | 97/24073 | 7/1997 |
| WO | 97/24074 | 7/1997 |
| WO | 97/24992 | 7/1997 |
| WO | 97/24993 | 7/1997 |
| WO | 97/24994 | 7/1997 |

| | | |
|---|---|---|
| WO | 97/25101 | 7/1997 |
| WO | 97/32551 | 9/1997 |
| WO | 97/33523 | 9/1997 |
| WO | 97/34540 | 9/1997 |
| WO | 97/41786 | 11/1997 |
| WO | 97/44071 | 11/1997 |
| WO | 97/48345 | 12/1997 |
| WO | 97/48346 | 12/1997 |
| WO | 98/07468 | 2/1998 |
| WO | 98/14131 | 4/1998 |
| WO | 98/17185 | 4/1998 |
| WO | 98/17186 | 4/1998 |
| WO | 98/27877 | 7/1998 |
| WO | 98/27879 | 7/1998 |
| WO | 98/27880 | 7/1998 |
| WO | 98/30144 | 7/1998 |
| WO | 98/34550 | 8/1998 |
| WO | 98/34558 | 8/1998 |
| WO | 98/38925 | 9/1998 |
| WO | 98/39038 | 9/1998 |
| WO | 99/00060 | 1/1999 |
| WO | 99/20185 | 4/1999 |
| WO | 99/20213 | 4/1999 |
| WO | 99/42037 | 8/1999 |
| WO | 99/44506 | 9/1999 |
| WO | 99/51155 | 10/1999 |
| WO | 99/51158 | 10/1999 |
| WO | 00/00098 | 1/2000 |
| WO | 00/09053 | 2/2000 |
| WO | 01/26570 | 4/2001 |
| WO | 01/87154 | 5/2001 |
| WO | 01/95819 | 12/2001 |
| WO | 02/36028 | 5/2002 |
| WO | 02/078557 | 10/2002 |
| WO | 02/102255 | 12/2002 |
| WO | 03/024305 | 3/2003 |
| WO | 03/024339 | 3/2003 |
| WO | 03/092477 | 11/2003 |
| WO | 2004/071278 | 8/2004 |
| WO | 2005/125287 | 12/2005 |
| WO | 2007/006000 | 1/2007 |
| WO | 2007/056729 | 5/2007 |

OTHER PUBLICATIONS

Costello et al., "Nd: YAG Laser Ablation of the Prostate as a Treatment for Benign Prostatic Hypertrophy", Lasers in Surgery and Medicine, vol. 12, pp. 121-124, 1992.

Rand et al., "Effect of Elecctrocautery on Fresh Human Articular Cartilage", J. Arthro. Surg., vol. 1, pp. 242-246, 1985.

O'Neill et al., "Percutaneous Plasma Discectomy Stimulates Repair in Injured Porcine Intervertebral Discs", Dept. of Orthopaedic Surgery, Dept. of Radiology University of California at San Francisco, CA, 3 pgs.

PCT International Search Report for PCT/US99/14685, 1 pg, Mailed Oct. 21, 1999.

PCT Notification of International Preliminary Examination Report for PCT/US99/14685, 4 pgs, Mailed Feb. 20, 2001.

PCT International Search Report for PCT/US98/22323, 1 pg, Mailed Mar. 3, 1999.

PCT Notification of International Preliminary Examination Report for PCT/US98/22323, 5 pgs, Mailed Nov. 28, 2000.

European Search Report for EP 98953859, 2 pgs, Jul. 2, 2001.

Supplementary European Search Report for EP 98953859, 3 pgs, Oct. 18, 2001.

PCT International Search Report for PCT/US99/18289, 1 pg, Mailed Dec. 7, 1999.

PCT Notification of International Preliminary Examination Report for PCT/US99/18289, 4 pgs, Mailed Jul. 7, 2000.

European Search Report for EP 99945039.8, 3 pgs, Oct. 1, 2001.

PCT International Search Report for PCT/US02/19261, 1 pg, Mailed Sep. 18, 2002.

PCT International Preliminary Examination Report for PCT/US02/19261, 3 pgs, Mar. 25, 2003.

PCT International Search Report for PCT/US02/29476, 1 pg, Mailed May 24, 2004.

PCT International Search Report for PCT/US03/13686, 1 pg, Mailed Nov. 25, 2003.

PCT International Search Report for PCT/US04/03614, 1 pg, Mailed Sep. 14, 2004.

PCT Written Opinion of the International Searching Authority for PCT/US04/03614, 4 pgs, Mailed Sep. 14, 2004.

EP Communication, European Examination Report for EP 98953859.0, 3 pgs, Jun. 14, 2004.

EP Communication, European Examination Report for EP 99945039.8, 5 pgs, May 10, 2004.

PCT Notification of International Search Report and Written Opinion for PCT/US06/26321, 8pgs, Mailed Apr. 25, 2007.

PCT Notification of the International Search Report and Written Opinion for PCT/US06/60618, 7pgs, Mailed Oct. 5, 2007.

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

Codman & Shurtleff, Inc. "The Malis Bipolar Coagulating and Bipolar Cutting System CMC-II" brochure, early, 2 pgs, 1991.

Codman & Shurtleff, Inc. "The Malis Bipolar Electrosurgical System CMC-III Instruction Manual" , 15 pgs, Jul. 1991.

Cook et al., "Therapeutic Medical Devices: Application and Design" , Prentice Hall, Inc., 3pgs, 1982.

Dennis et al. "Evolution of Electrofulguration in Control of Bleeding of Experimental Gastric Ulcers," Digestive Diseases and Sciences, vol. 24, No. 11, 845-848, Nov. 1979.

Dobbie, A.K., "The Electrical Aspects of Surgical Diathermy, Bio Medical Engineering" *Bio-Medical Engineering* vol. 4, pp. 206-216, May 1969.

Elsasser, V.E. et al., "An Instrument for Transurethral Resection without Leakage of Current" *Acta Medicotechnica* vol. 24, No. 4, pp. 129-134, 1976.

Geddes, "Medical Device Accidents: With Illustrative Cases" CRC Press, 3 pgs, 1998.

Honig, W., "The Mechanism of Cutting in Electrosurgery" *IEEE* pp. 58-65, 1975.

Kramolowsky et al. "The Urological App of Electorsurgery" *J. of Urology* vol. 146, pp. 669-674, 1991.

Kramolowsky et al. "Use of 5F Bipolar Electrosurgical Probe in Endoscopic Urological Procedures" *J. of Urology* vol. 143, pp. 275-277, 1990.

Lee, B et al. "Thermal Compression and Molding of Artherosclerotic Vascular Tissue with Use" JACC vol. 13(5), pp. 1167-1171, 1989.

Letter from Department of Health to Jerry Malis dated Jan. 24, 1991, 3 pgs.

Letter from Department of Health to Jerry Malis dated Jul. 25, 1985, 1 pg.

Letter from Jerry Malis to FDA dated Jul. 25, 1985, 2 pgs.

Lu, et al., "Electrical Thermal Angioplasty: Catheter Design Features, in Vitro Tissue Ablation Studies and in Vitro Experimental Findings," *Am J. Cardiol* vol. 60, pp. 1117-1122, Nov. 1, 1987.

Malis, L., "Electrosurgery, Technical Note," *J. Neursurg.*, vol. 85, pp. 970-975, Nov. 1996.

Malis, L., "Excerpted from a seminar by Leonard I. Malis, M.D. at the 1995 American Association of Neurological Surgeons Meeting," 1pg, 1995.

Malis, L., "Instrumentation for Microvascular Neurosurgery" *Cerebrovascular Surgery*, vol. 1, pp. 245-260, 1985.

Malis, L., "New Trends in Microsurgery and Applied Technology," *Advanced Technology in Neurosurgery*, pp. 1-16, 1988.

Malis, L., "The Value of Irrigation During Bipolar Coagulation" See ARTC 21602, 1 pg, Apr. 9, 1993.

Nardella, P.C., *SPIE* 1068: pp. 42-49, Radio Frequency Energy and Impedance Feedback, 1989.

O'Malley, Schaum's Outline of Theory and Problems of Basic Circuit Analysis, McGraw-Hill, $2^{nd}$ Ed., pp. 3-5, 1992.

Olsen MD, Bipolar Laparoscopic Cholecstectomy Lecture (marked confidential), 12 pgs, Oct. 7, 1991.

Pearce, John A. "Electrosurgery", pp. 17, 69-75, 87, John Wiley & Sons, New York, 1986.

Pearce, John A., "Electrosurgery", Handbook of Biomedical Engineering, chapter 3, Academic Press Inc., N.Y., pp. 98-113, 1988.

Piercey et al., "Electrosurgical Treatment of Experimental Bleeding Canine Gastric Ulcers" *Gastroenterology* vol. 74(3), pp. 527-534, 1978.

Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.

Ramsey et al., "A Comparison of Bipolar and Monopolar Diathermy Probes in Experimental Animals", *Urological Research* vol. 13, pp. 99-102, 1985.

Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.

Shuman, "Bipolar Versus Monopolar Electrosurgery: Clinical Applications," *Dentistry Today*, vol. 20, No. 12, 7 pgs, Dec. 2001.

Slager et al. "Spark Erosion of Arteriosclerotic Plaques" *Z. Kardiol.* 76:Suppl. 6, pp. 67-71, 1987.

Slager et al. "Vaporization of Atherosclerotice Plaques by Spark Erosion" *JACC* 5(6): pp. 1382-1386, Jun. 1985.

Stoffels, E. et al., "Investigation on the Interaction Plasma-Bone Tissue", E-MRS Spring Meeting, 1 pg, Jun. 18-21, 2002.

Stoffels, E. et al., "Biomedical Applications of Plasmas", Tutorial presented prior to the 55th Gaseous Electronics Conference in Minneapolis, MN, 41 pgs, Oct. 14, 2002.

Stoffels, E. et al., "Plasma Interactions with Living Cells", Eindhoven University of Technology, 1 pg, 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg, Nov. 28, 2003.

Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engineering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of *Escherichia coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and Streptococcus Mutans", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for in Vivo Medical Treatment: Recent Developments and Perspectives", Plasma Sources Sci. Technol. 15, pp. S169-S180, Oct. 6, 2006.

Swain, C.P., et al., "Which Electrode, A Comparison of four endoscopic methods of electrocoagulation in experimental bleeding ulcers" *Gut* vol. 25, pp. 1424-1431, 1987.

Tucker, R. et al. "A Comparison of Urologic Application of Bipolar Versus Monopolar Five French Electrosurgical Probes" *J. of Urology* vol. 141, pp. 662-665, 1989.

Tucker, R. et al. "In vivo effect of 5 French Bipolar and Monopolar Electrosurgical Probes on the Porcine Bladder" *Urological Research* vol. 18, pp. 291-294, 1990.

Tucker, R. et al., "Demodulated Low Frequency Currents from Electrosurgical Procedures," *Surgery, Gynecology and Obstetrics*, 159:39-43, 1984.

Tucker, R. et al., Abstract P14-11, p. 248, "A Bipolar Electrosurgical Turp Loop", Nov. 1989.

Valley Forge Scientific Corp., "Summary of Safety and Effective Information from 510K", 2pgs, 1991.

Valley Forge's New Products, Clinica, 475, 5, Nov. 6, 1991.

Valleylab SSE2L Instruction Manual, 11 pgs, Jan. 6, 1983.

Valleylab, Inc. "Valleylab Part No. 945 100 102 A" Surgistat Service Manual, pp. 1-46, Jul. 1988.

Wattiez, Arnaud et al., "Electrosurgery in Operative Endoscopy," Electrosurgical Effects, Blackwell Science, pp. 85-93, 1995.

Wyeth, "Electrosurgical Unit" pp. 1181-1202, 2000.

UK Search Report for GB0805061.9 1 pg, Jul. 15, 2008.

BiLAP IFU 910033-002 Rev A for BiLAP Model 3527, L-Hook; BiLAP Model 3525, J-Hook; BiLAP Model 3529, High Angle, 2 pgs, Nov. 30, 1993.

BiLAP IFU 910026-001 Rev A for BiLAP Model 3525, J-Hook, 4 pgs, May 20, 1991.

BiLAP Generator Settings, Jun. 1991.

Tucker et al. "The interaction between electrosurgical generators, endoscopic electrodes, and tissue," Gastrointestinal Endoscopy, vol. 38, No. 2, pp. 118-122, 1992.

Buchelt, et al. "Excimer Laser Ablation of Fibrocartilage: An in Vitro and in Vivo Study", Lasers in Surgery and Medicine, vol. 11, pp. 271-279, 1991.

Costello et al., "Nd: YAG Laser Ablation of the Prostate as a Treatment for Benign Prostatic Hypertrophy", Lasers in Surgery and Medicine, vol. 12, pp. 121-124, 1992.

Hardy et al., "Regional Myocardial Blood Flow and Cardiac mechanics in dog Hearts with CO2 laser-induced Intramyocardial Revascularization", Basic Research in cardiology 85:179-196, 1990.

Mirhoseini et al., "New Concepts in Revascularization of the Myocardium", Ann Thorac Surg 45:415-420, 1988.

Mirhoseini et al., "Revascularization of the heart by Laser", J. of Microsurgery 2:253-260, 1981.

Mirhoseini et al., "Transmyocardial Laser Revascularization: A Review", J. of Clinical Laser medicine & Surgery 11 (1) :15-19, 1993.

Mirhoseini et al., "Transventricular Revascularization by Laser", Lasers in Surgery and Medicine 2:187-198, 1982.

Rand et al., "Effect of Elecctrocautery on Fresh Human Articular Cartilage", J. Arthro. Surg., vol. 1, pp. 242-246, 1985.

Walter et al., "Treatment of Acute Mycardial Infarction by Transmural Blood Supply from the Ventricular Cavity", Erop. Surgery Res. 3:130-138, 1971.

Whittaker et al., "Transmural Channels Can Protect Ischemic Tissue", Circulation 93(1):143-152, Jan. 1, 1996.

EP Search Report for EP01124768 2 pgs, Nov. 30, 2001.

EP Search Report for EP01935650 10 pgs, Mailed Jul. 26, 2006.

EP Search Report for EP01935650 8 pgs, Mailed May 3, 2005.

EP Search Report for EP02768969 3 pgs, Mailed Feb. 12, 2007.

EP Search Report for EP03762238 3 pgs, Mailed Jun. 2, 2006.

EP Search Report for EP94916716 2 pgs, Oct. 29, 1996.

EP Search Report for EP96941386 2 pgs, Nov. 27, 1998.

EP Search Report for EP98952032 2 pgs, Nov. 24, 2000.

PCT International Search Report for PCT/US00/07718 1 pg, Mailed Sep. 5, 2000.

PCT International Search Report for PCT/US01/16006 1pg, Mailed Aug. 14, 2001.

PCT International Search Report for PCT/US02/31640 1 pg, Mailed May 23, 2003.
PCT International Search Report for PCT/US03/04689 1 pg, Mailed Sep. 26, 2003.
PCT International Search Report for PCT/US03/12790 1pg, Mailed Aug. 12, 2003.
PCT International Search Report for PCT/US03/20574 1 pg, Mailed May 25, 2005.
PCT International Search Report for PCT/US04/22803 1 pg, Mailed Apr. 29, 2005.
PCT International Search Report for PCT/US05/07038 1 pg, Mailed Sep. 2, 2005.
PCT International Search Report for PCT/US94/05168, 1 pg, Mailed Oct. 18, 1994.
PCT International Search Report for PCT/US98/20768 1pg, Mailed Jan. 20, 1999.
PCT International Search Report for PCT/US98/22327 1 pg, Mailed Feb. 9, 1999.
PCT IPER for PCT/US01/16006 3pgs, Apr. 16, 2002.
PCT IPER for PCT/US98/22327 4pgs, Aug. 27, 2000.
PCT Written Opinion for PCT/US04/22803 3pgs, Mailed Apr. 29, 2005.
PCT Written Opinion for PCT/US05/07038 3pgs, Mailed Sep. 2, 2005.
Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual" , 15 pgs, Jul. 1991.
Cook et al., "Therapeutic Medical Devices: Application and Design" , Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artheroscletotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malls dated Jul. 25, 1985, 1 pg.
Letter from Jerry Malis to FDA dated Jul. 25, 1985, 2 pgs.
Lu, et al., "Electrical Thermal Angioplasty: Catheter Design Features, in Vitro Tissue Ablation Studies and in Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atheroscletotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and Streptococcus Mutans", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for in Vivo Medical Treatment: Recent Developments and Perspectives", Plasma Sources Sci. Technol. 15, pp. S169-S180, Oct. 6, 2006.

Swain, C.P., et al., "Which Electrode, A Comparison of four endoscopic methods of electrocoagulation in experimental bleeding ulcers" *Gut* vol. 25, pp. 1424-1431, 1987.

Tucker, R. et al. "A Comparison of Urologic Application of Bipolar Versus Monopolar Five French Electrosurgical Probes" *J. of Urology* vol. 141, pp. 662-665, 1989.

Tucker, R. et al. "In vivo effect of 5 French Bipolar and Monopolar Electrosurgical Probes on the Porcine Bladder" *Urological Research* vol. 18, pp. 291-294, 1990.

Tucker, R. et al., "Demodulated Low Frequency Currents from Electrosurgical Procedures," *Surgery, Gynecology and Obstetrics*, 159:39-43, 1984.

Tucker, R. et al., Abstract P14-11, p. 248, "A Bipolar Electrosurgical Turp Loop", Nov. 1989.

Valley Forge Scientific Corp., "Summary of Safety and Effective Information from 510K", 2pgs, 1991.

Valley Forge's New Products, Clinica, 475, 5, Nov. 6, 1991.

Valleylab SSE2L Instruction Manual, 11 pgs, Jan. 6, 1983.

Valleylab, Inc. "Valleylab Part No. 945 100 102 A" Surgistat Service Manual, pp. 1-46, Jul. 1988.

Wattiez, Arnaud et al., "Electrosurgery in Operative Endoscopy," Electrosurgical Effects, Blackwell Science, pp. 85-93, 1995.

Wyeth, "Electrosurgical Unit" pp. 1181-1202, 2000.

EP Search Report for EP 03736488 3 pgs, Mailed Jun. 25, 2009.

PCT International Search Report for PCT/US96/18505, 3 pgs, Mailed Jan. 17, 1997.

PCT Notif of the Int'l Search Report and Written Opinion for PCT/US09/67001 6 pgs, Mailed Jan. 29, 2010.

UK Search Report for GB0921635.9 3pgs, Apr. 12, 2010.

EP Search Report for EP 07118068 3pgs, Mailed Dec. 27, 2010.

EP Search Report for EP 04778347 4pgs, Feb. 22, 2011.

\* cited by examiner

ROTARY ELECTROSURGICAL APPARATUS AND METHODS THEREOF

CROSS REFERENCE TO RELATED APPLICATIONS

This application is a 35 U.S.C. 371 application of International Application No. PCT/US04/22803 filed Jul. 16, 2004, which claims the benefit of U.S Provisional Application No. 60/488,134 filed Jul. 16, 2003.

BACKGROUND OF THE INVENTION

The present invention relates generally to the field of electrosurgery, and more particularly to methods and apparatus for the controlled removal of a target tissue during an electrosurgical procedure. The present invention further relates to an apparatus including a rotating member housed within a shaft, and an active electrode adapted to electrosurgically remove tissue, via molecular dissociation of tissue components, during rotation of the rotating member.

Surgical instruments that mechanically remove tissue by contact with a rotating burr, blade, etc., are well known in the art, and have been used for both open and closed surgical procedures. Such instruments, however, suffer from a number of disadvantages. Firstly, the cutting edge (e.g., blade) tends to dull fairly rapidly during use, such that it may be necessary to change the cutting component of the instrument during the course of a single procedure. As a result, the time and cost of performing the procedure is increased. A further disadvantage associated with rotary cutting, drilling, and shaving devices is that they typically result in substantial bleeding as the tissue is removed. Such bleeding must be controlled in order to prevent obstruction of the surgeon's view of the surgical site. Attempts have been made to control bleeding by the application of a tourniquet, by administering the vasoconstrictor epinephrine, and, in the case of certain arthroscopic procedures, by pressurizing the joint cavity. Each of these approaches to control bleeding is associated with one or more disadvantages. Establishment of hemostasis following mechanical removal of tissue has also been achieved by the application of a separate electrocautery device to bleeding blood vessels. However, the use of an ancillary electrocautery device typically involves removal of the mechanical cutting device, thereby necessitating a delay in coagulating the bleeding vessels, and consequently requires additional time, and associated costs, for completing the procedure as a whole.

A number of surgical devices are known that include a movable shaving or cutting mechanism and which also incorporate an electrode for cauterizing or cutting tissue. For example, U.S. Pat. No. 5,941,876, to Nardella et al., discloses an inner, rotating tissue-affecting element comprising an electrically conductive shaft, and a non-conductive material disposed over predetermined regions of an outer surface of the shaft, wherein a distal portion of the outer surface of the shaft is exposed to define an active electrode surface. Removal of tissue is by the mechanical action of the rotating shaft and by electrosurgical energy delivered to the tissue by an energized cutting edge. U.S. Pat. No. 6,036,681 (to Hooven) discloses a method and apparatus for morcelating tissue. The apparatus includes an outer tube and an inner tube that may be caused to rotate by a motor. Various electrode configurations are disclosed for cutting, slicing, or otherwise sub-dividing excised tissue via RF electrical energy.

Other devices having both a movable cutting device and an electrode are disclosed, e.g., in U.S. Pat. No. 5,810,809 to Rydell; U.S. Pat. No. 6,193,715 to Wrublewski et al.; and U.S. Pat. No. 6,032,673 to Savage et al. See also, U.S. Pat. No. 4,815,462 to Clark. All patents, patent applications, and publications mentioned in this application are incorporated by reference in their entirety.

There is a need for an instrument that removes target tissue electrosurgically in a highly controlled manner, and which can also provide hemostasis at the surgical site. There is a further need for an inexpensive, yet reliable and effective rotary tissue removal device that removes tissue by the molecular dissociation of tissue components during the application of electrical energy to an electrode of the instrument.

SUMMARY OF THE INVENTION

The present invention provides systems, apparatus, and methods for the controlled removal of a patient's tissue during an electrosurgical procedure. According to one aspect of the invention, there is provided an instrument having a rotating member and an active electrode. The instrument removes tissue by the application of electrical energy to the target tissue via the active electrode as the rotating member rotates within an outer shaft. The systems and methods of the present invention are applicable to a broad range of procedures, including procedures which involve the removal or shaping of relatively hard connective tissue.

In one aspect, the present invention provides an electrosurgical instrument for treating a target tissue, the instrument including a fixed shaft having a longitudinal void therein, a tissue removal port disposed at the shaft distal end portion, an elongate rotating member housed longitudinally within the longitudinal void of the shaft, and an active electrode disposed at the instrument distal end. The active electrode is adapted to electrosurgically remove at least a portion of the target tissue via molecular dissociation of target tissue components as the rotating member rotates within the shaft.

The rotating member is coupled to a drive motor for driving rotation of the rotating member within the shaft. A proximal end of the rotating member may be coupled to a hub, and the hub may be housed within a handle affixed to the proximal end of the shaft. The drive motor may be integral with the instrument. Alternatively, the drive motor may be remote from the instrument and coupled to the rotating member via a flexible transmission line. The drive motor is adapted to drive the rotating member, during removal of tissue, at speeds in the range of from about 5 to 750 rpm, and often at speeds as low as about 20 to 90 rpm.

According to alternative embodiments of the invention, the active electrode may be affixed to the outer shaft, or may be mounted on the rotating member. The active electrode may be a discrete electrode having an electrode lead attached directly thereto for coupling the active electrode to an electrosurgical generator. Alternatively, the active electrode may be an exposed, non-insulated portion of a larger, electrically conductive component. Typically, the instrument is a bipolar device having a return electrode disposed at the working or distal end of the instrument. The instrument may further include a dedicated coagulation electrode adapted for coagulating severed blood vessels and for inducing hemostasis at the surgical site. Alternatively, the active electrode or the return electrode may be adapted for inducing hemostasis.

The instrument typically further includes an aspiration element or unit for aspirating excess or unwanted materials from the surgical site during a procedure. The aspiration element is in fluid communication at its distal end with the tissue removal port. The aspiration element typically includes an aspiration lumen terminating distally in one or more aspiration ports. The aspiration element may be coupled at its proximal end to a suitable vacuum source. In one embodiment, the aspiration lumen may comprise a discrete tube disposed within a longitudinal channel of the rotating member.

The tissue removal port is typically arranged laterally at the distal end portion of the shaft. The instrument is configured such that a portion of the rotating member traverses the tissue removal port as the rotating member rotates within the shaft. The tissue removal port is typically rounded, substantially circular, or oval, and has a width equal to or less than the internal diameter of the shaft. According to one aspect of the invention, one or both of the active electrode and the return electrode are disposed adjacent to, or contiguous with, the tissue removal port.

According to one embodiment of the invention, there is provided an instrument including a shaft having a shaft distal end portion, an active electrode disposed on the shaft distal end portion, and a return electrode disposed on the shaft distal end portion and spaced from the active electrode. The instrument further includes a tissue removal port at the shaft distal end portion, and a rotating member housed longitudinally within a longitudinal void of the shaft. The rotating member is adapted to rotate axially within the shaft, such that the rotating member distal end traverses the tissue removal port during each revolution of the rotating member within the shaft.

In one embodiment, the active electrode is affixed to an external surface of the shaft distal end portion at a location adjacent to, or contiguous with, the tissue removal port. In one embodiment, at least a distal portion of the rotating member has an arcuate cross-sectional shape. According to one aspect of the invention, the rotating member distal end includes a leading edge adapted to guide a portion of a target tissue towards the active electrode as the rotating member rotates within the shaft. The active electrode is adapted to remove a portion of the target tissue as the target tissue is guided towards the active electrode by the leading edge of the rotating member. Typically, removal of the target tissue is effected via molecular dissociation of target tissue components upon application of a suitable high frequency voltage to the active electrode.

According to one embodiment of the invention, there is provided a system including an electrosurgical instrument coupled to an electrosurgical generator or power supply. The system is adapted for treating a target tissue during an electrosurgical procedure. In one embodiment, the instrument is adapted for both removal of tissue and for maintaining hemostasis at the surgical site during tissue removal. Typically, the instrument includes an outer shaft having a shaft distal end portion, a tissue removal port at the shaft distal end portion, and an elongate rotating member housed within the shaft, wherein the rotating member has a distal end configured to traverse the tissue removal port as the rotating member rotates within the shaft.

The instrument further includes an active electrode adapted to electrosurgically remove a portion of the target tissue during each revolution of the rotating member, and a return electrode disposed at the instrument distal end. The electrosurgical generator is coupled to the instrument, e.g., via a connector cable coupled to a connection block, the latter housed within a proximal handle of the instrument. The electrosurgical generator is adapted for applying a high frequency voltage between the active and return electrodes. The electrosurgical generator may be switchable (e.g., via a foot pedal) between an ablation mode and a sub-ablation mode. The active electrode is adapted to electrosurgically remove at least a portion of the target tissue, via the molecular dissociation of target tissue components, upon application of the high frequency voltage.

According to another embodiment of the invention, there is provided an electrosurgical instrument for ablating a target tissue and for inducing hemostasis adjacent to the target tissue. The instrument includes a shaft having a shaft distal end portion, a tissue removal port at the shaft distal end portion, a rotating member housed within the shaft, wherein the rotating member is adapted to rotate within the shaft. The instrument further includes an electrode support disposed on the rotating member distal end, and a discrete active electrode disposed on the electrode support. In one embodiment, the electrode support extends distally from the rotating member distal end, and the active electrode is affixed to a distal end of the electrode support, wherein the active electrode is configured to traverse the tissue removal port as the rotating member rotates within the shaft. In one embodiment of the invention, the active electrode comprises an arcuate conductive element, e.g., comprising a curved metal wire. The arcuate conductive element may be suspended across a gap between a distal end of the electrode support and the rotating member. The active electrode is adapted to electrosurgically remove at least a portion of the target tissue, via the molecular dissociation of target tissue components, as the active electrode traverses the tissue removal port.

In one aspect, the present invention provides a method for the controlled removal of a target tissue at a surgical site during an electrosurgical procedure, wherein the method comprises providing an electrosurgical instrument having a shaft and a tissue removal port at a distal end portion of the shaft. The instrument further includes a rotating member adapted to rotate within the shaft, and an active electrode disposed on an external surface of the shaft distal end portion. The shaft distal end portion is positioned in at least close proximity to the target tissue. While the instrument is so positioned, the rotating member is driven such that the rotating member rotates within the shaft distal end, and the rotating member repeatedly traverses the tissue removal port.

While the rotating member is being driven within the shaft, a high frequency voltage is applied between the active electrode and a return electrode. The active electrode is adapted for removing tissue upon application of the high frequency voltage between the active and return electrodes, whereby the target tissue is sequentially removed as the rotating member rotates within the shaft. In one embodiment, the rotating member distal end is adapted to guide a portion of the target tissue towards the active electrode as the rotating member rotates within the shaft. The rotating member may be driven at a speed in the range of from about 5 to 750 rpm, perhaps in the range of from about 6 to 600 rpm, and in some embodiments from about 20 to 90 rpm, and often about 60 rpm.

According to one aspect of the invention, a fluid, such as isotonic saline, may be delivered to the target tissue or to the working end of the electrosurgical instrument during a procedure. Such a fluid may be delivered via an ancillary device, or via a fluid delivery element integral with the instrument. In some embodiments, the fluid serves to flush the target site and to improve the surgeon's visibility of the surgical field. An electrically conductive fluid (e.g., saline) may also promote initiation and maintenance of a plasma in the vicinity of the active electrode, and thereby enable tissue ablation via the Coblation® phenomenon or process. The Coblation® process is described hereinbelow.

In another aspect, the present invention is concerned with treating (e.g., ablating) a target tissue on or within a patient's body using an instrument including one or more active electrodes coupled to a power supply. In the case of tissue ablation, a portion of the instrument working end (e.g., the shaft distal end adjacent the tissue removal port) is positioned in at least close proximity to the target tissue, and the rotating member is rotatively driven within the shaft while the power supply is operating in an ablation mode. In the ablation mode, a high frequency voltage applied to the active electrode(s) is sufficient to vaporize an electrically conductive fluid (e.g., a gel, saline, synovial fluid) between the active electrode(s) and the tissue. Within the vaporized fluid a plasma is formed, and charged particles (e.g., electrons) of the plasma cause the molecular dissociation of target tissue components. This molecular dissociation is accompanied by the volumetric removal of at least a portion of the tissue, and can be used to resect fragments of target tissue without the application of a substantial mechanical force to the tissue from a moving component of the instrument. This ablation process (known as Coblation®) can be precisely controlled to effect the volumetric removal of tissue as thin as 10 microns to 150 microns. A more complete description of the Coblation® phenomenon can be found in commonly assigned U.S. Pat. No. 5,697,882, the disclosure of which is incorporated by reference herein in its entirety.

An electrosurgical instrument (e.g., a probe or catheter) according to the present invention generally includes a shaft having proximal and distal end portions, an active electrode and a return electrode at the working end of the instrument, and a connection block for coupling the active and return electrodes to a source of high frequency electrical energy (e.g., an electrosurgical generator or power supply). The return electrode is typically spaced from the active electrode(s) by an electrically insulating material. In some embodiments, the active electrode is disposed on a discrete electrode support, e.g., comprising a ceramic, a glass, or a silicone rubber. In other embodiments, the active and return electrodes are spaced apart by a portion of the tissue removal port.

In one aspect of the present invention, the active and return electrodes may be spaced apart such that the distance between the active and return electrodes does not vary. The electrodes may be parallel to one another. Also, the electrodes may be curved wherein each electrode has the same curvature or serpentine path such that the distance between them remains constant The active electrode will usually have a smaller exposed surface area than the return electrode such that, during application of a voltage to the active electrode, the current density is much higher at the active electrode than at the return electrode. The active electrode(s) may comprise a single active electrode, a plurality of active electrodes, or an electrode array.

The instrument may further include an aspiration element adapted to remove excess or unwanted materials (e.g., saline, resected tissue fragments, and ablation by-products) from the surgical site via an aspiration stream. The instrument may still further include one or more aspiration electrodes adapted for digesting resected tissue fragments or other debris that may be drawn towards, or through, the aspiration element via the aspiration stream.

For a further understanding of the nature and advantages of the invention, reference should be made to the following description taken in conjunction with the accompanying drawings.

DESCRIPTION OF SPECIFIC EMBODIMENTS

Figure 1:
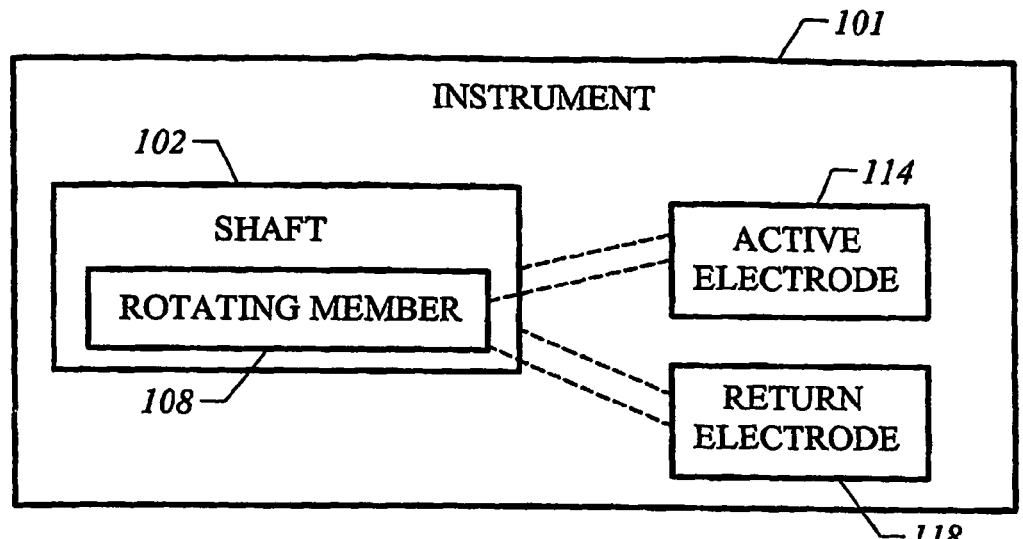
FIG. 1 is a block diagram schematically representing an instrument incorporating a rotating member housed within a shaft, according to the present invention.

The present invention provides systems, apparatus, and methods for selectively applying electrical energy to a target tissue of a patient, and for the controlled removal of the target tissue via molecular dissociation of target tissue components. The invention is particularly suited to remove or sequentially remove a portion of the target tissue as a rotating member rotates within a shaft. The instrument includes a tissue removal port arranged at a distal end portion of the shaft, and at least one active electrode disposed at the working end of the instrument. The active electrode(s) are typically disposed either at a distal portion of the shaft adjacent to the tissue removal port, or on the rotating member. In the latter situation, the active electrode(s) are configured to traverse the tissue removal port as the rotating member rotates within the shaft.

Systems, apparatus, and methods of the invention are applicable to a broad range of procedures, including: open procedures, intravascular procedures, urological procedures, laparoscopy, arthroscopy, cardiac procedures (including thoracoscopy), dermatologic, orthopedic, gynecological, otorhinolaryngological, spinal, and neurologic procedures, as well as in oncology, and the like. Tissues which may be treated by apparatus and methods of the present invention include, without limitation, connective tissue, including bone, articular cartilage, meniscal cartilage, ligaments, and tendons; prostate tissue; leiomyomas (fibroids) of the uterus; gingival tissues and mucosal tissues of the mouth; tumors; scar tissue; and myocardial tissue; as well as collagenous tissue of the eye, and the dermis and epidermis of the skin.

The present invention is useful for arthroscopic procedures of the knee, shoulder, elbow, etc., including the ablation, re-shaping, or re-surfacing of articular cartilage, and the partial removal or modification of a damaged meniscal cartilage of the knee. The invention may also be applicable to various spinal procedures, such as laminectomy/discectomy procedures for treating herniated disks, posterior lumbosacral and cervical spine fusions, treatment of scoliosis associated with vertebral disease, and foraminotomies to relieve nerve root compression.

The present invention is also useful for procedures in the head and neck, e.g., targeting the ear, mouth, pharynx, larynx, esophagus, nasal cavity and sinuses. These procedures may be performed through the mouth or nose using speculae or gags, or using endoscopic techniques, such as functional endoscopic sinus surgery (FESS). The present invention may also be used for collagen shrinkage, ablation, and/or hemostasis, e.g., during procedures for treating snoring and obstructive sleep apnea; for gross tissue removal, such as tonsillectomies, adenoidectomies, tracheal stenosis and vocal cord polyps and lesions; or for the resection or ablation of facial tumors or tumors within the mouth and pharynx, such as glossectomies, laryngectomies, acoustic neuroma procedures, and nasal ablation procedures.

Apparatus and methods of the present invention may also be useful for cosmetic and plastic surgery procedures. For example, the present invention may be employed for skin tissue removal, e.g., for the removal of pigmentations, vascular lesions, scars, tattoos, etc., as well as for other surgical procedures on the skin, such as tissue rejuvenation, wrinkle removal, etc.

In one embodiment of the present invention, radio frequency (RF) electrical energy is applied to one or more active electrodes of an instrument, in the presence of an electrically conductive fluid, to remove and/or modify at least a portion of a target tissue or organ. Depending on the specific procedure, the present invention may be used to: (1) ablate tissue, including soft tissue, bone, and cartilage; (2) cut or resect tissue; (3) shrink or contract collagen containing tissue; and/or (4) coagulate, occlude, and sever blood vessels.

In one aspect of the invention, a target tissue may be volumetrically removed or ablated by applying a high frequency voltage between one or more active electrode(s) and one or more return electrode(s) to develop high electric field intensities in the vicinity of the target tissue. The high electric field intensities adjacent the active electrode(s) result in electric field-induced ablation via molecular dissociation of target tissue components (as opposed to ablation via thermal evaporation or carbonization of tissue in many conventional electrosurgical procedures). In particular, applicant believes that the target tissue is volumetrically removed through molecular disintegration of larger organic molecules into smaller molecules and/or atoms, such as hydrogen, oxygen, oxides of carbon, hydrocarbons, and nitrogen compounds. This molecular disintegration completely removes the target tissue, as opposed to dehydrating the tissue by the removal of cellular fluids, the latter typical of many prior art electrosurgical desiccation and vaporization processes. An electrosurgical process for the volumetric removal of tissue via molecular dissociation of tissue components at relatively low temperatures (cool ablation) has been termed Coblation®.

In one aspect, the present invention involves applying a high frequency voltage between one or more active electrode(s) and one or more return electrode(s) to develop high electric field intensities in the vicinity of the target tissue to heat the target tissue in a highly controlled manner. In one embodiment, the high frequency voltage is sufficient to vaporize an electrically conductive fluid over at least a portion of the active electrode surface, in a region between the distal tip of the active electrode(s) and the target tissue, to form an ionized vapor, or plasma, layer. The electrically conductive fluid may be a gas or a liquid, such as isotonic saline, blood, extracellular or intracellular fluid, or a viscous fluid, such as a gel. Since the vapor layer, or vaporized region, has a relatively high electrical impedance, it minimizes current flow into the electrically conductive fluid.

A more complete description of the plasma state can be found in Introduction to Plasma Physics, (1995), by R. J. Goldston and P. H. Rutherford (Published by IOP Pub), the complete disclosure of which is incorporated by reference herein. When the density of the vapor layer surrounding an energized active electrode (or within a bubble formed in the adjacent electrically conductive fluid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Once the charge particles in the plasma layer attain sufficient energy, they accelerate towards the adjacent target tissue. Energy evolved by energetic electrons of the plasma layer (e.g., on the order of 3.5 eV to 5 eV) can subsequently bombard a molecular component of the target tissue and break its bonds, thereby dissociating the molecule into free radicals, which may then combine to form gaseous or liquid species (i.e., Coblation® by-products).

Plasmas may be formed by heating a gas and ionizing the gas by driving an electric current through it, or by transmitting radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing substantially non-thermal molecular breakdown of target tissue components.

While not being bound by theory, applicant believes that the principal mechanism of tissue removal in the Coblation® mechanism of the present invention is energetic electrons or ions that have been energized in a plasma adjacent to the active electrode(s). Under the conditions described herein, energetic electrons and photons may be discharged from the vapor layer and to the surface of the target tissue, causing molecular dissociation of target tissue components. The Coblation® phenomenon is further described in commonly assigned U.S. Pat. No. 5,697,882, the disclosure of which is incorporated by reference herein in its entirety.

The present invention is particularly useful for removing or ablating a target tissue while minimizing or avoiding damage to underlying tissue, e.g., bone or nerves, beneath the surface of the target tissue. In the present invention, the Coblation® process allows for the controlled, precise removal of tissue. This feature minimizes collateral damage to underlying non-target tissue. Damage to non-target tissue may be further minimized by monitoring a temperature condition of the target tissue or at the working end of the instrument adjacent to the target tissue. Apparatus and methods for temperature monitoring during electrosurgical procedures are described in U.S. Provisional Patent Application Ser. 60/445,405, the disclosure of which is incorporated by reference herein in its entirety.

An electrosurgical instrument of the invention typically includes a shaft having a proximal end and a distal or working end portion. One or more active electrodes are disposed at the distal end of the instrument. A return electrode is typically spaced from the active electrode(s), e.g., by an electrically insulating material or electrode support. In some embodiments, a dedicated coagulation electrode may be disposed at the distal tip or apex of the instrument.

For percutaneous procedures, e.g., for arthroscopic treatment of synovial joints, the shaft may have a suitable diameter and length to allow the surgeon to reach the target tissue by delivering the shaft through a percutaneous opening in the patient. Thus, the shaft may have a length in the range of, for example, from about 5 cm to 25 cm, and a diameter in the range of from about 0.5 mm to 5 mm. In some embodiments, the shaft may also be introduced through rigid or flexible endoscopes.

Typically, instruments of the invention are adapted for coupling to an electrosurgical generator or RF power supply, wherein the power supply is capable of operation in an ablation mode (for ablating tissue), or a sub-ablation mode (for coagulating or otherwise modifying the tissue). In some embodiments, electrosurgical instruments of the invention will include one or more electrode leads by which the electrode(s) are connected to a connection block. The connection block is adapted for coupling the electrode(s) to the generator or power supply. Typically, the connection block includes a plurality of pins for coupling to the power supply via a connector cable.

In some embodiments, instruments of the invention may include a limited usage switch for rendering the instrument inoperable after a pre-set number of usage cycles. The connection block may include a voltage reduction element, e.g., a resistor, which may be coupled between two of the plurality of pins of the connection block. In one embodiment, the voltage reduction element is a component of the limited usage mechanism. A description of apparatus and methods for restricting the number of usage cycles of electrosurgical instruments may be found in commonly assigned co-pending U.S. Patent Application Ser. Nos. 60/375,979 and 10/139, 154, filed Apr. 24, 2002 and May 3, 2002, respectively, the disclosures of which are incorporated by reference herein in their entirety. See also, U.S. patent application Ser. No. 10/139,117.

Instruments of the invention may use a single active electrode or an electrode array disposed at a working end of the instrument. In the latter embodiment, the electrode array may include a plurality of independently current-limited and/or power-controlled active electrodes to apply electrical energy selectively to the target tissue. Apparatus incorporating independently current-limited and/or power-controlled active electrodes is described in commonly assigned U.S. Pat. No. 6,312,408, the disclosure of which is incorporated by reference herein in its entirety.

The voltage applied between the active and return electrodes will typically be in the radio frequency (RF) range, having a frequency of between about 5 kHz and 20 MHz, usually being between about 30 kHz and 2.5 MHz, and often between about 100 kHz and 200 kHz. The RMS (root mean square) voltage applied will usually be in the range from about 5 volts RMS to 1500 volts RMS, typically being in the range of from about 10 volts RMS to 900 volts RMS, and often in the range of from about 20 volts RMS to 500 volts RMS, depending on the active electrode size and geometry, the operating frequency, the particular procedure or desired effect on the target tissue (e.g., ablation, contraction, coagulation), and the type (composition) of the tissue. Typically, the peak-to-peak voltage will be in the range of 10 to 2000 volts, usually in the range of 20 to 1200 volts, and often in the range of about 40 to 800 volts (again, depending on the electrode size, the operating frequency, and the operation mode). Voltage parameters for various electrosurgical procedures are presented in commonly assigned U.S. Pat. No. 6,235,020, the disclosure of which is incorporated by reference herein in its entirety.

The voltage is typically delivered in a series of voltage pulses or alternating current of time varying voltage amplitude having a sufficiently high frequency (e.g., on the order of 5 kHz to 20 MHz) such that the voltage is effectively applied continuously (as compared with, e.g., certain lasers adapted for shallow depths of tissue necrosis, which are generally pulsed at about 10 Hz to 20 Hz). In addition, the duty cycle (i.e., cumulative time in any one-second interval that energy is applied) is on the order of about 50% for apparatus of the present invention, as compared with a duty cycle of about 0.0001% for many pulsed lasers.

The application of a suitable high frequency voltage between the active and return electrodes effects cutting, removal, ablation, shaping, contracting, coagulating, or other form of modification of the target tissue. The tissue volume over which energy is dissipated may be precisely controlled, for example, by the use of a multiplicity of small active electrodes whose effective diameters or principal dimensions typically range from about 5 mm to 0.01 mm, and usually from about 2 mm to 0.05 mm. In these embodiments, electrode areas for both circular and non-circular electrode terminals will have a contact area (per active electrode) of 25 $mm^2$ or less, typically being in the range of from about 5 $mm^2$ to 0.005 $mm^2$. In general, the use of relatively small diameter active electrodes increases the electric field intensity, and reduces the extent or depth of tissue heating as a consequence of the divergence of current flux lines which emanate from the exposed surface of each active electrode.

A preferred power supply of the present invention delivers a high frequency current selectable to generate average power levels ranging from several milliwatts to tens of watts per electrode, depending on the volume of target tissue being treated, and/or the maximum allowed temperature selected for the probe tip. The power supply allows the user to select the voltage level according to the specific requirements of a particular procedure, e.g., arthroscopic surgery, other endoscopic surgery, FESS procedure, dermatological procedure, or open surgery. A description of a power supply adapted for electrosurgery can be found in commonly assigned U.S. Pat. No. 6,142,992, the disclosure of which is incorporated by reference herein in its entirety.

A current flow path between the active and return electrodes may be provided by delivering an electrically conductive fluid (e.g., an electrically conductive gel or saline) to the working end of the instrument. Such a fluid may be provided by an ancillary fluid delivery device, or by a fluid delivery element integral with the instrument. To provide a suitable current flow path between the active and return electrodes, an electrically conductive fluid delivered to the working end of the instrument should have a suitable electrical conductivity, typically at least 0.2 millisiemens per centimeter (mS/cm), usually greater than 2 mS/cm, and often greater than 10 mS/cm. In one embodiment, the electrically conductive fluid is isotonic saline, which has a conductivity of about 17 mS/cm. In other embodiments, electrically conductive fluids having electrical conductivity values much higher than that of isotonic saline may also be used. A discussion of various electrically conductive fluids, having a range of electrical conductivity values, suitable for use in electrosurgery appears in commonly assigned U.S. Pat. No. 6,149,620, the disclosure of which is incorporated by reference herein in its entirety. Delivery of an electrically conductive fluid to provide a current flow path between the active and return electrodes is described in commonly assigned U.S. Pat. No. 5,697,281, the disclosure of which is also incorporated by reference herein in its entirety.

In some procedures, it may also be necessary to retrieve or aspirate excess or unwanted materials, e.g., saline, ablation by-products, from the target site. For example, in arthroscopic procedures it may be desirable to aspirate resected fragments of connective tissue (e.g., articular cartilage) removed from within a synovial joint. In addition, it may be desirable to aspirate excess saline, blood, mucus, gaseous ablation by-products, etc., from the surgical site. Accordingly, systems of the invention may include an aspiration element or lumen, which may be integral with the instrument, for aspirating materials from the target site.

Furthermore, in some embodiments the instrument may include one or more aspiration electrode(s) (or digestion electrode(s)) for ablating, or reducing the volume of, resected tissue fragments that are aspirated into the aspiration lumen. Instruments incorporating aspiration electrodes are described in commonly assigned U.S. Pat. Nos. 6,238,391 and 6,254,600, the disclosures of which are incorporated by reference herein in their entirety.

Referring now to the drawings, FIG. 1 is a block diagram schematically representing an electrosurgical instrument 101 adapted for applying electrical energy to a target tissue of a patient, and for the controlled removal of the target tissue during a procedure performed on the patient. Instrument 101 includes a shaft 102 which houses a rotating member 108. Shaft 102 is typically an elongate tube having a longitudinal bore or void therein. Rotating member 108 is adapted to rotate within shaft 102. In one embodiment, rotating member 108 extends the entire length of shaft 102 and terminates in a proximal handle or handpiece (e.g., FIG. 4). Instrument 101 typically includes a tissue removal port at the distal end of shaft 102 (e.g., FIG. 4).

Rotating member 108 may be coupled directly to a drive motor, e.g., a DC motor housed within the handle. Alternatively, rotating member 108 may be coupled to a remote drive motor via a flexible transmission line, as is well known in the art. Such a remote drive motor may either be integral with an electrosurgical generator, wherein the generator is adapted to supply a high frequency voltage to the electrodes of instrument 101, as well as rotational force (torque) to rotating member 108 (e.g., FIG. 2). Alternatively, the remote drive motor may comprise a self-contained unit having a separate power supply (e.g., FIG. 4). In one embodiment, the drive motor may be powered by a battery pack.

Typically, instrument 101 is a bipolar electrosurgical device, and includes an active electrode 114 and a return electrode 118 disposed at the working or distal end of instrument 101 (see, e.g., FIGS. 5A-9C). Dashed lines in FIG. 1 indicate that active electrode 114 and return electrode 118 may be disposed on either shaft 102 or on rotating member 108. Thus, according to various embodiments of the invention, one or both of active electrode 114 and return electrode 118 may be disposed on rotating member 108. Similarly, one or both of active electrode 114 and return electrode 118 may be disposed on shaft 102. Electrode(s) mounted on rotating member 108 typically move in a substantially circular motion when rotating member 108 rotates within shaft 102. In contrast, electrode(s) mounted on shaft 102 are in fixed relation thereto when rotating member 108 rotates within shaft 102.

Rotating member 108 may comprise an electrically insulating material (e.g., various plastics). Alternatively, member 108 may comprise an electrically conductive material coated or encased within an electrically insulating material. In situations where at least one of active electrode 114 and return electrode 118 are disposed on rotating member 108, one or both of active electrode 114 and return electrode 118 may be defined by an exposed, non-insulated portion of rotating member 108. Alternatively, one or both of active electrode 114 and return electrode 118 may comprise a discrete electrode having an electrode lead for coupling to the generator.

Similarly, shaft 102 may comprise an electrically insulating material; or shaft 102 may comprise an electrically conductive material encased within an electrically insulating layer. In situations where at least one of active electrode 114 and return electrode 118 are disposed on shaft 102, one or both of active electrode 114 and return electrode 118 may be defined by an exposed, non-insulated portion of shaft 102. Or, at least one of active electrode 114 and return electrode 118 may comprise a discrete electrode having an electrode lead for coupling to the generator.

Figure 2:
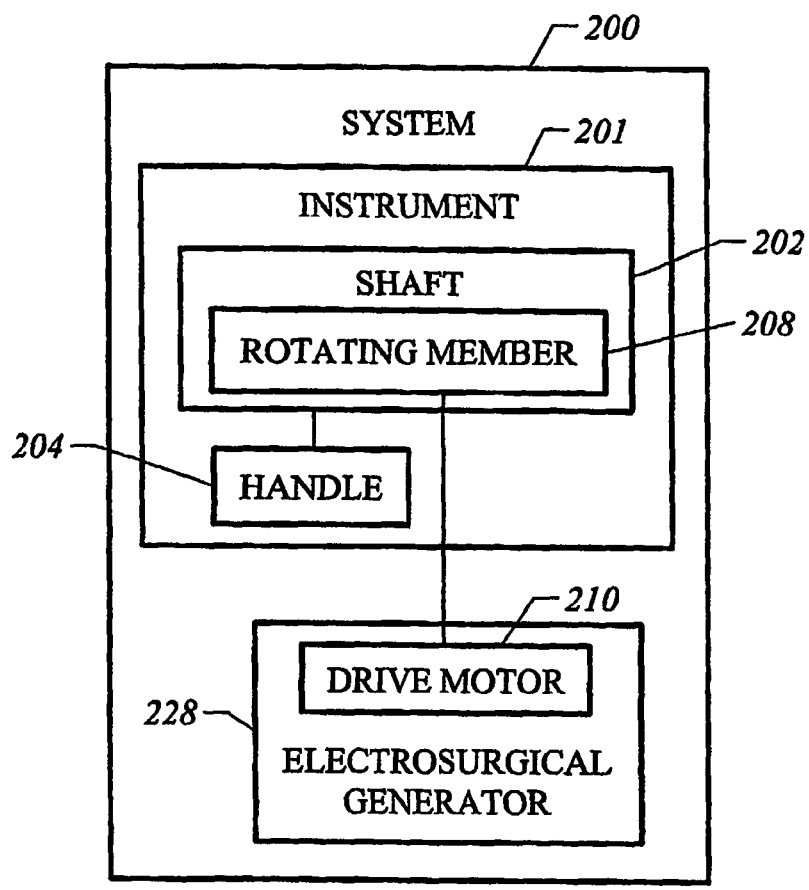
FIG. 2 is a block diagram schematically representing an electrosurgical system including an instrument having a rotating member coupled to a drive motor, according to one embodiment of the invention.

FIG. 2 illustrates an electrosurgical system 200, according to one embodiment of the invention. System 200 includes an instrument 201 such as an electrosurgical probe. Instrument 201 includes a shaft 202 having a rotating member 208 rotatably housed therein. A handle 204 is typically affixed to a proximal end of shaft 202. Instrument 201 includes at least one active electrode and at least one return electrode (not shown in FIG. 2). System 200 further includes an electrosurgical generator 228. Typically, generator 228 comprises a RF power supply for supplying a RF alternating-current voltage to instrument 201. As shown, generator 228 includes an integral drive motor 210 coupled to rotating member 208. In alternative embodiments, the drive motor may be a self-contained unit separate from generator 228, or may be housed within handle 204.

Rotating member 208 is typically driven by drive motor 210 to rotate within shaft 202 at a speed in the range of from about 5 to 750 rpm, more typically from about 6 to 600 rpm, usually from about 20 to 90 rpm, and often about 60 rpm. The speed of rotation of rotating member 208 can be adjusted via a suitable control mechanism, for example, via a switch mounted on the handle of the instrument, via a control unit integral with the generator, or may be controlled remotely e.g., via a foot pedal.

Figure 3A:
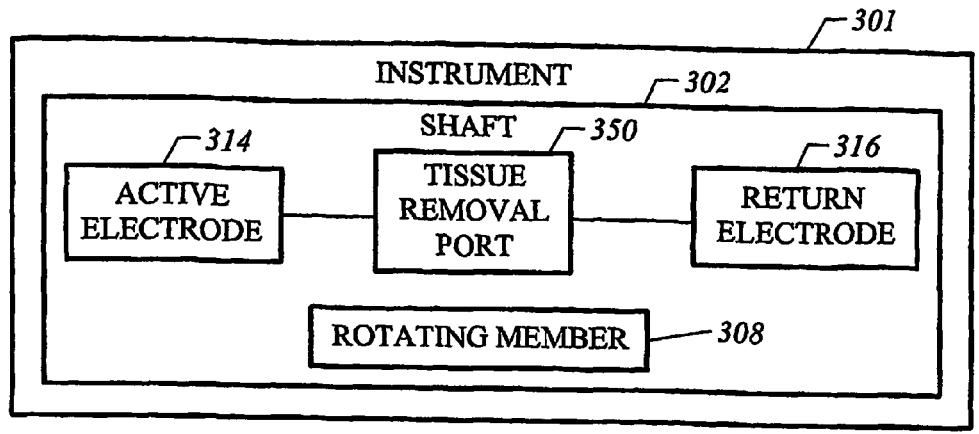
FIGS. 3A-C are block diagrams, each schematically representing an electrosurgical instrument including a rotating member housed within a shaft, according to three different embodiments of the invention.
Figure 3B:
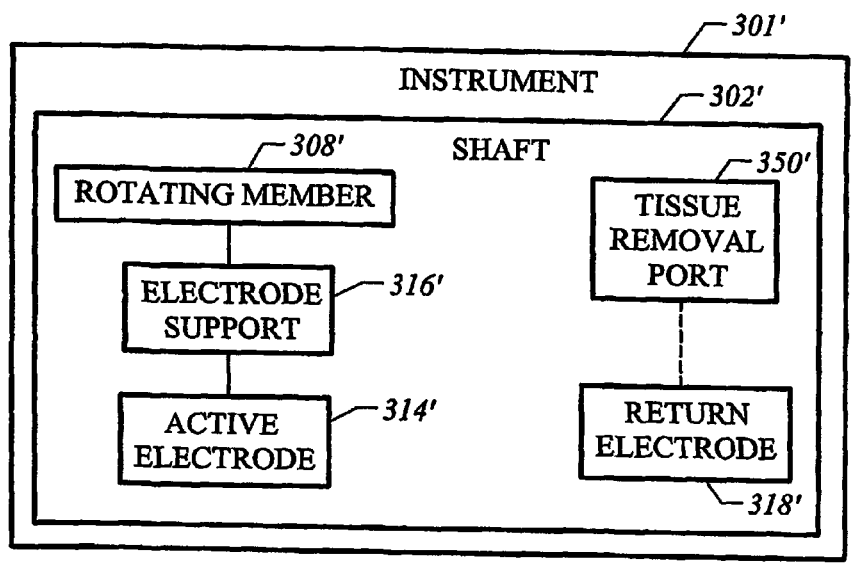
Figure 3C:
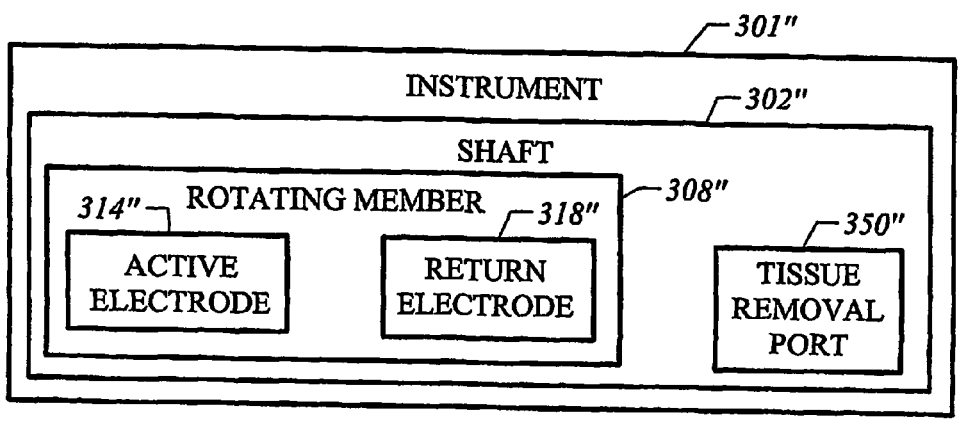

FIGS. 3A-C are block diagrams, each schematically representing an electrosurgical instrument including a rotating member housed within a shaft, according to three different embodiments of the invention. In the embodiment of FIG. 3A, instrument 301 includes an elongate outer shaft 302 and a rotating member 308 housed within a longitudinal void of shaft 302. Rotating member 308 is adapted to rotate within shaft 302. Instrument 301 further includes a tissue removal port 350 arranged on shaft 302. An active electrode 314 and a return electrode 318 are disposed on shaft 302. In one embodiment, active electrode 314 and return electrode 318 are disposed adjacent to tissue removal port 350. As an example, tissue removal port 350 may be rectangular, serpentine, rounded, substantially circular, or oval in outline. Tissue removal port 350 has a width, w equal or less than the width of rotating member 308. The length of port 350 is typically in the range of from about 0.5-5 times w (i.e., from 0.5 w to 5 w), and usually from about 1-2 times w. A distal portion of rotating member 308 is configured to traverse tissue removal port 350 as rotating member 308 rotates within shaft 302. According to one aspect of the invention, the distal portion of rotating member 308 is adapted to guide target tissue towards at least one of active electrode 314 and return electrode 318 as the distal portion of rotating member 308 traverses port 350.

FIG. 3B shows an instrument 301' incorporating a rotating member 308' configured to rotate within a shaft 302', according to another embodiment of the invention. An electrode support 316' is disposed on rotating member 308', and an active electrode 314' is disposed on electrode support 316'. In some embodiments, rotating member 308' comprises an electrically insulating material, active electrode 314' may be disposed directly on rotating member 308', and electrode support 316' may be omitted. Instrument 301' further includes a tissue removal port 350', and a return electrode 318' disposed on shaft 302' (e.g., FIGS. 9A-C). In one embodiment, return electrode 318' lies adjacent to tissue removal port 350'. Instrument 301' is configured such that active electrode 314' traverses tissue removal port 350' during each revolution of rotating member 308'. Typically, tissue removal port 350' is disposed at a distal end portion of shaft 302'.

FIG. 3C shows an instrument 301" incorporating a rotating member 308", according to another embodiment of the invention. Rotating member 308" is configured to rotate within shaft 302". A tissue removal port 350" is arranged on shaft 302". In the embodiment of FIG. 3C, both active electrode 314" and return electrode 318" are disposed on rotating member 308". Accordingly, when member 308" rotates, both active electrode 314" and return electrode 318" undergo substantially circular motion. Typically, instrument 301" is configured such that both active electrode 314" and return electrode 318" traverse tissue removal port 350" during each revolution of rotating member 308" (e.g., FIG. 8B).

Figure 4:
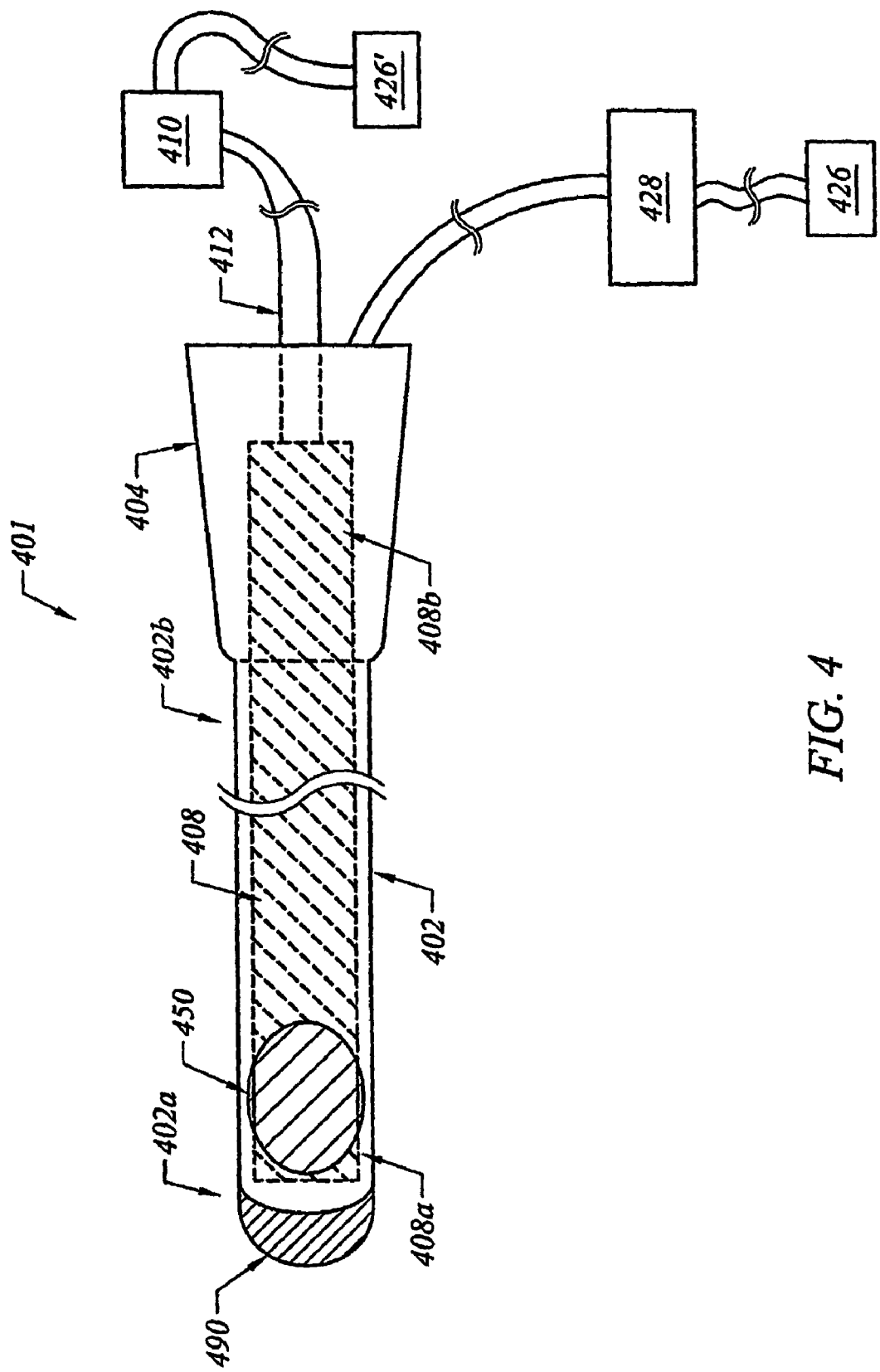
FIG. 4 is a partial longitudinal sectional view of an instrument coupled to an electrosurgical generator and a drive motor, according to one embodiment of the invention.

FIG. 4 schematically represents an electrosurgical system, according to one embodiment of the invention. The system of FIG. 4 includes an instrument or electrosurgical probe 401 which is shown in partial longitudinal sectional view. Instrument 401 includes a shaft 402 having a shaft distal end portion 402a, and a shaft proximal end portion 402b affixed to a handle 404. A rotating member 408 housed within shaft 402 includes a distal end 408a and a proximal end 408b. Rotating member proximal end 408b extends into handle 404. Rotating member 408 may have various cross-sectional shapes. In some embodiments, the rotating member is arcuate or C-shaped in cross-section (e.g., FIG. 5B). In other embodiments, the rotating member may be in the form of a cylinder (e.g., FIG. 7B).

Typically, instrument 401 includes an active electrode and a return electrode (neither of which are shown in FIG. 4) disposed at the working or distal end of instrument 401. The active electrode is typically disposed at a location such that tissue removal port 450 and the active electrode are substantially equidistant from the distal tip of shaft 402. Also, the port may be positioned at the distal tip such that portion of the distal tip is open (e.g., see FIG. 5F). Instrument 401 is coupled to an electrosurgical generator 428 and a drive motor 410. Generator 428 is adapted to supply a high frequency voltage between the active and return electrodes of instrument 401. Instrument 401 may be conveniently coupled to generator 428 via a connection block (not shown) housed within handle 404.

As shown, rotating member distal end 408a terminates distal to tissue removal port 450. However, in some embodiments, the rotating member distal end may terminate proximal to the tissue removal port, wherein an active electrode, which extends distally from the rotating member, lies adjacent to the tissue removal port (e.g., FIGS. 7A-B).

As shown, instrument 401 further includes a coagulation electrode 490 adapted for coagulating severed blood vessels to induce hemostasis at the surgical site. Although, FIG. 4 shows coagulation electrode 490 disposed at the distal tip of shaft 402, other configurations are also within the scope of the invention. In some embodiments, the instrument may lack a dedicated coagulation electrode, in which case at least one of the active electrode and the return electrode may serve to coagulate tissue.

Generator 428 is capable of operation in an ablation mode (for ablating tissue), or a sub-ablation mode (for coagulating or otherwise modifying the tissue). For the ablation of relatively hard connective tissue, the voltage supplied by generator 428 is typically in the range of from about 200 volts RMS to 1500 volts RMS. In the sub-ablation mode (e.g., for coagulation or hemostasis), the voltage applied by generator 428 is typically in the range of from about 10 to 1000 volts RMS, usually from about 20 to 500 volts RMS, and often from about 20 to 150 volts RMS. One or more foot pedal controls 426 coupled to generator 428 can be used to conveniently adjust the power level of generator 428, and to switch generator 428 between the ablation and sub-ablation modes. An electrosurgical apparatus having foot pedal controls is described fully in commonly assigned U.S. Pat. No. 6,264,650, the disclosure of which is incorporated by reference herein in its entirety.

Again with reference to FIG. 4, drive motor 410 is coupled to rotating member proximal end 408b via a flexible transmission line 412. A foot pedal 426' coupled to drive motor 410 may be used to control the speed of rotation of rotating member 408. In an alternative embodiment, the drive motor may be integral with the generator (e.g., FIG. 2), in which case the speed of the rotating member may be adjusted by a foot pedal coupled to the generator.

Figure 5A:
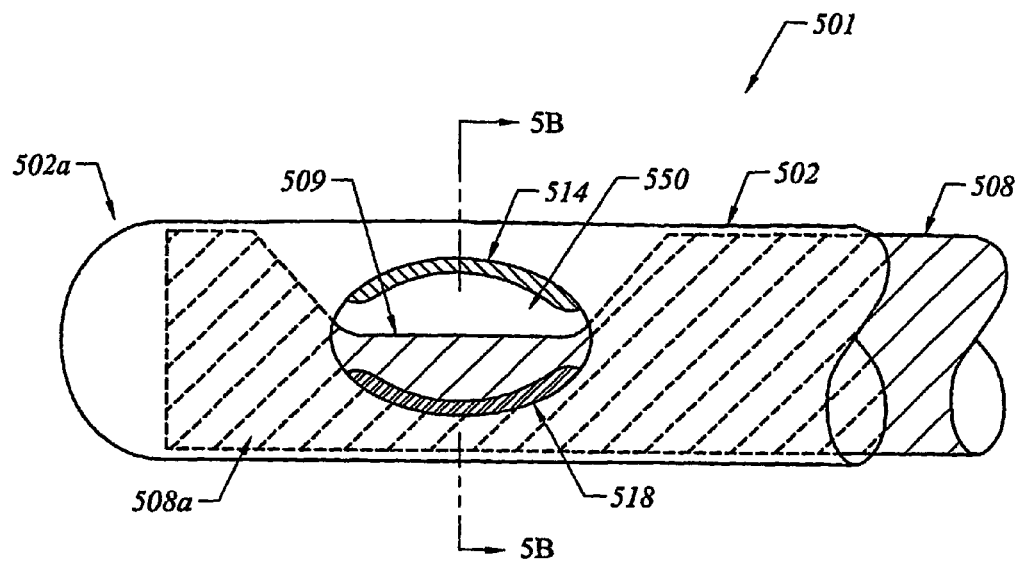
FIG. 5A is a partial longitudinal sectional view of the working or distal end of an instrument, according to one embodiment of the invention.
Figure 5B:
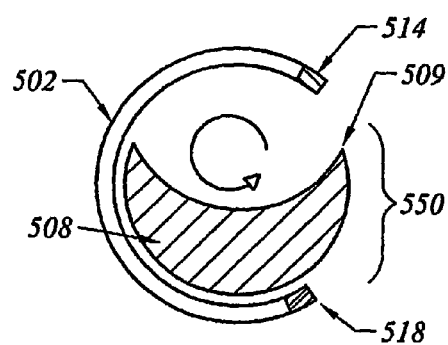
FIG. 5B is a transverse sectional view taken along the lines 5B-5B of FIG. 5A.

FIG. 5A is a partial longitudinal sectional view of the working end of an instrument 501 having a pair of electrodes 514, 518 fixedly mounted on a hollow shaft 502, according to one embodiment of the invention. FIG. 5B is a sectional view taken along the lines 5B-5B of FIG. 5A. With reference to FIGS. 5A-B, instrument 501 includes a rotating member 508 housed within shaft 502. A tissue removal port 550 is arranged laterally at shaft distal end portion 502a. First and second electrodes 514, 518 are disposed at the perimeter of tissue removal port 550. As shown, first and second electrodes 514, 518 appear as elongate shapes arranged on diametrically opposite sides of tissue removal port 550. However, other electrode shapes and configurations are also possible under the invention.

Perhaps as best seen in FIG. 5B, rotating member 508 has an arcuate distal end 508a which includes a leading edge 509. When member 508 rotates counter-clockwise (as indicated by the circular arrow in FIG. 5B), leading edge 509 approaches first electrode 514 as leading edge 509 traverses tissue removal port 550. In some embodiments, leading edge 509 is adapted to guide target tissue towards first electrode 514. Leading edge 509, or a portion of member 508 in the vicinity of leading edge 509, may be adapted, e.g., by being shaped or having a textured surface, to provide friction between member 508 and the target tissue. In the embodiment of FIGS. 5A-B, rotating member 508 typically comprises a non-conducting material, such as various polymers or plastics, e.g., a polycarbonate, a polyetherimide, polyetheretherketone (PEEK), other thermoplastic or thermosetting materials having suitable properties, e.g., torsional strength, flexibility, and electrical insulation properties.

Again with reference to FIGS. 5A-B, first and second electrodes 514, 518 may be discrete electrodes, each having an electrode lead for coupling first and second electrodes 514, 518 to opposite poles of a high frequency power supply. Such a power supply is adapted for applying a high frequency voltage between first and second electrodes 514, 518. Target tissue is sequentially removed as leading edge 509 repeatedly approaches first electrode 514. Typically, such removal of tissue is effected by electrosurgical molecular dissociation of target tissue components upon application of the high frequency voltage between first and second electrodes 514, 518. First electrode 514 may be an active electrode, and second electrode 518 may be a return electrode. The relative location of the active and return electrodes may be reversed without departing from the scope of the invention. In addition, the direction of rotation of rotating member 508 may be reversed (i.e., from counter-clockwise to clockwise). Also, "mirror image" versions of various instruments described herein may be prepared, e.g., with respect to the location of the active electrode relative to the direction of rotation of the rotating member. Such "mirror image" devices are also within the scope of the invention.

Figure 5C:
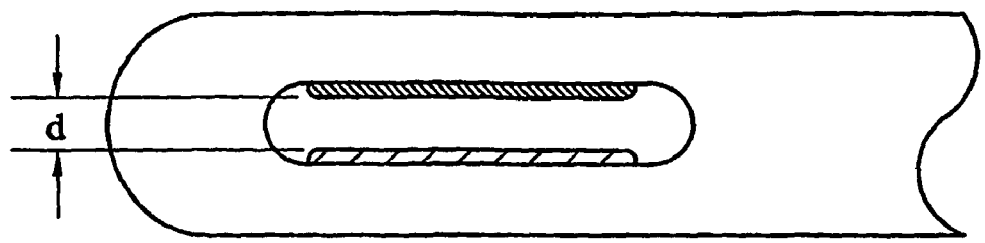
FIGS. 5C-5E are partial side views of the distal end of an instrument showing active and return electrodes separated by a constant distance (d)
Figure 5D:
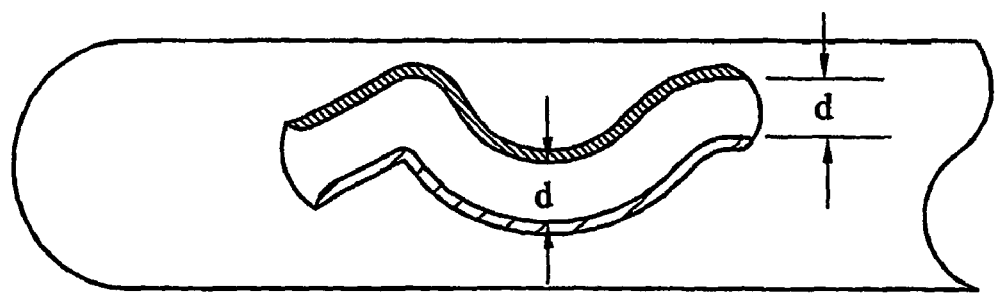
Figure 5E:
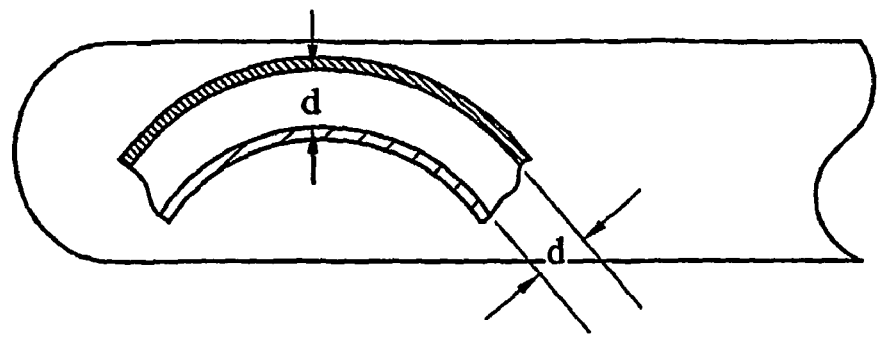

As mentioned above, the shape of the port may vary widely. FIGS. 5C-5E illustrate examples of the distal end of a shaft with various port shapes including respectively rectangular (or slotted), serpentine, and arcuate. Also, each of the ports shown in FIGS. 5C-5E have constant spacing between the active electrode and the return electrode. However, it is also contemplated that the spacing between the active and return electrodes may vary.

Figure 5F:
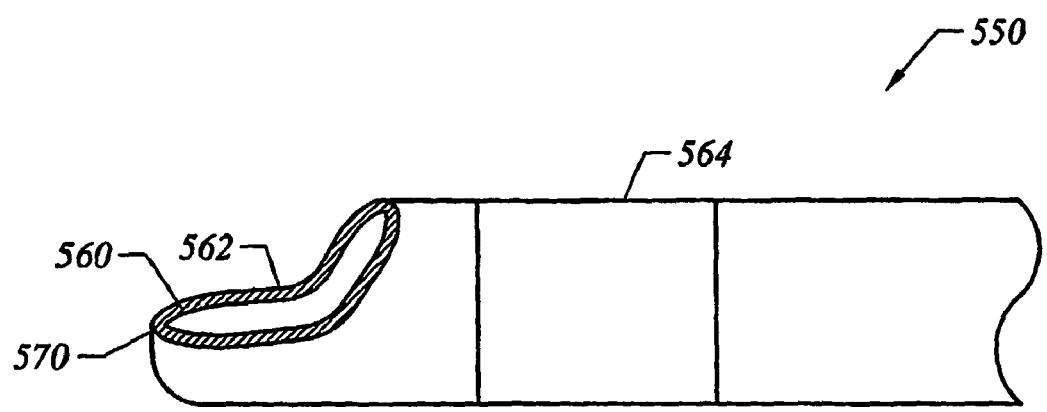
FIG. 5F is a partial side view of the distal end of an instrument having a port at the distal tip.

FIG. 5F illustrates yet another embodiment of the present invention illustrating a distal portion of a shaft 550 having a distal port 560. The distal portion has a jaw bone shape. An active electrode 562 is shown disposed along the perimeter or edge of the port. The active electrode may be a wire, ring, plate, screen, coating, etc. Also, there may be a plurality of active electrodes along or attached in some manner to the jaw bone distal tip. A return electrode 564 is spaced apart from the active electrode. The return electrode 564 may be an annular ring or clip as well as an uncovered portion of an electrically conducting tube. A voltage difference is applied between the active and return electrode to ablate tissue that contacts or comes near the active electrode. An axially rotating member (not shown) may extend through a lumen of the shaft 550 to manipulate tissue against the active electrode thereby cutting or ablating tissue. Notably, this device may operate at low rpm speeds (e.g., rpm less than 90 and perhaps less than 20) as well as shave tissue along the distal wall 570. The electrode configuration and voltage control may be carried out as described above such that a plasma is formed that molecularly dissociates tissue components. However, the invention is not so limited. Energy may be delivered from such a device to coagulate, ablate, heat, or otherwise affect the tissue.

Additionally, in a procedure, the device of the present invention may form an angle of approach with tissue to be removed up to 90 degrees. In other words, the instrument may be axially inserted straight into tissue. Additionally, the angle of approach may be less than 45 degrees and a painting motion may be carried out to remove target tissue.

Figure 6A:
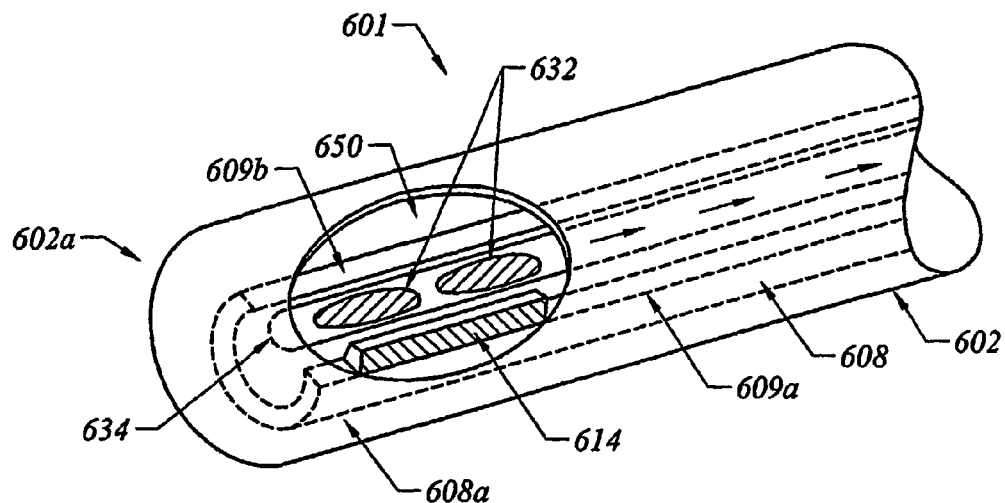
FIG. 6A is a perspective view of a distal end of an electrosurgical instrument having a rotating member housed within a shaft.

FIG. 6A is a perspective view of a working or distal end of an electrosurgical instrument, according to another embodiment of the invention. Instrument 601 includes an outer shaft 602 having a shaft distal end 602a. A longitudinal void within shaft 602 accommodates a rotating member 608 having a distal end 608a. As shown, rotating member 608 has an arcuate or C-shaped cross-sectional shape. Rotating member 608 may have substantially the same cross-sectional shape as it extends proximally. Alternatively, rotating member 608 may adopt a circular cross-sectional shape as it extends proximally, either as an open cylinder or as a rod (closed cylinder). An aperture formed in shaft distal end 602a defines a tissue removal port 650. Tissue removal port 650 is shown as having an oval shape, although other shapes are also within the scope of the invention.

Figure 6B:
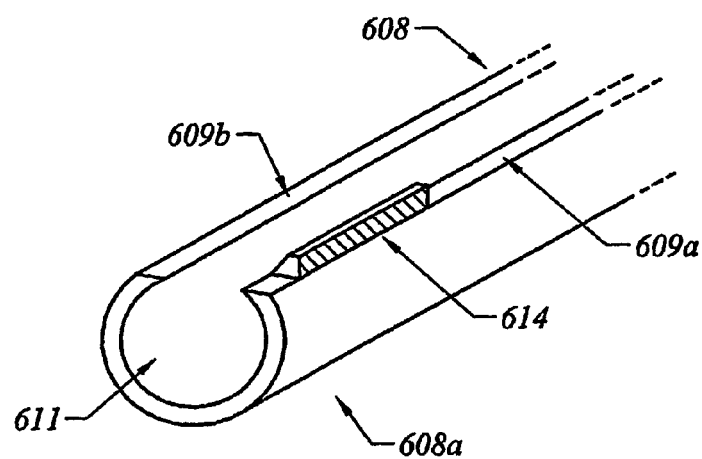
FIG. 6B is a perspective view of the distal end portion of the rotating member of FIG. 6A shown in isolation from the shaft, according to another embodiment of the invention.

Instrument 601 further includes an active electrode 614 mounted on a first longitudinal edge 609a of rotating member 608 (FIG. 6B). Active electrode 614 is shown in FIGS. 6A-B as having a rectangular shape. However, other active electrode geometries and configurations are also contemplated under the invention. Instrument 601 still further includes a return electrode disposed at the working end of instrument 601. The return electrode is not shown in FIG. 6A for the sake of clarity. As an example, the return electrode may be a discrete electrode, e.g., a metal band affixed to shaft distal end 602a Alternatively, shaft 602 may comprise an electrically conductive material encased within an electrically insulating layer, and the return electrode may be defined by an exposed, non-insulated portion of shaft distal end 602a. In other embodiments, the return electrode may be disposed on rotating member 608 (e.g., FIGS. 3C, 8A-B).

FIG. 6B is a perspective view of the distal end portion of rotating member 608 of FIG. 6A shown in isolation from shaft 602, and showing longitudinal void 611. Groove 611 accommodates an aspiration element adapted for removing excess or unwanted materials from the vicinity of tissue removal port 650. In the embodiment of FIGS. 6A-B, the aspiration element includes a discrete aspiration lumen 634 disposed within the longitudinal groove of rotating member 608. As shown in FIG. 6A, a plurality of aspiration ports 632 are arranged within the distal portion of aspiration lumen 634, such that aspiration port 632 are in fluid communication with tissue removal port 650. Other configurations for an aspiration unit are also possible under the invention. Electrosurgical apparatus having an aspiration element is described in commonly assigned U.S. Pat. No. 6,238,391, the disclosure of which is incorporated by reference herein in its entirety.

Again with reference to FIGS. 6A-B, rotating member 608 includes first and second longitudinal edges 609a, 609b, respectively. Active electrode 614 is mounted longitudinally on first longitudinal edge 609a. In one embodiment, rotating member 608 rotates counter-clockwise within shaft 602, such that first longitudinal edge 609a serves as a leading edge as first edge 609a traverses tissue removal port 650. In an alternative embodiment, active electrode 614 may be mounted on second longitudinal edge 609b, and rotating member 608 may be adapted to rotate clockwise such that second edge 609b traverses port 650 from right to left as the instrument is viewed from its proximal end. Aspiration lumen 634 is omitted from FIG. 6B for the sake of clarity.

Figure 7A:
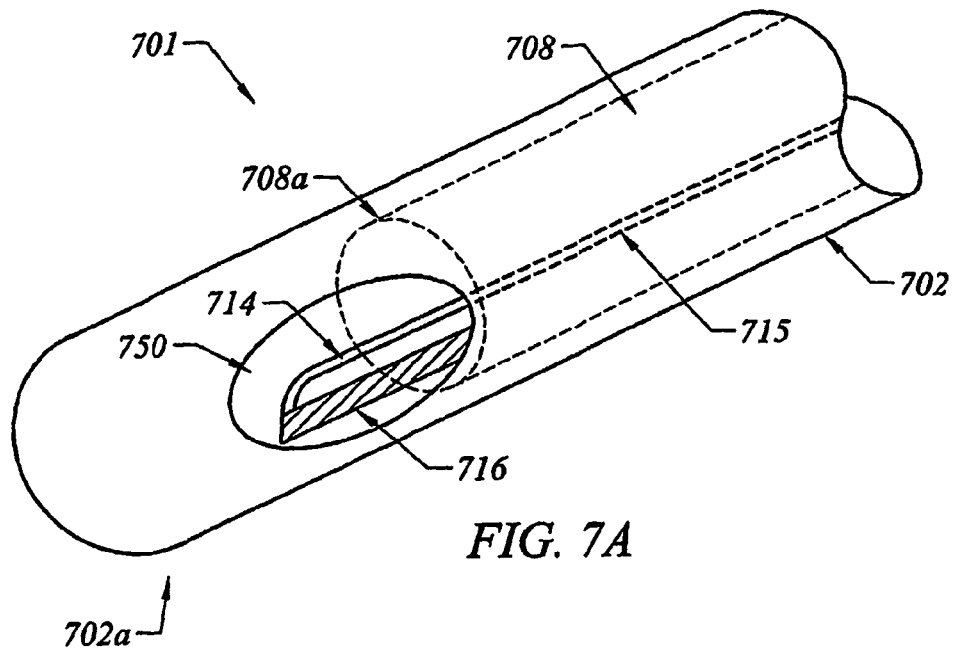
FIG. 7A is a perspective view of the distal end of an electrosurgical instrument having a shaft and a rotating member within the shaft.
Figure 7B:
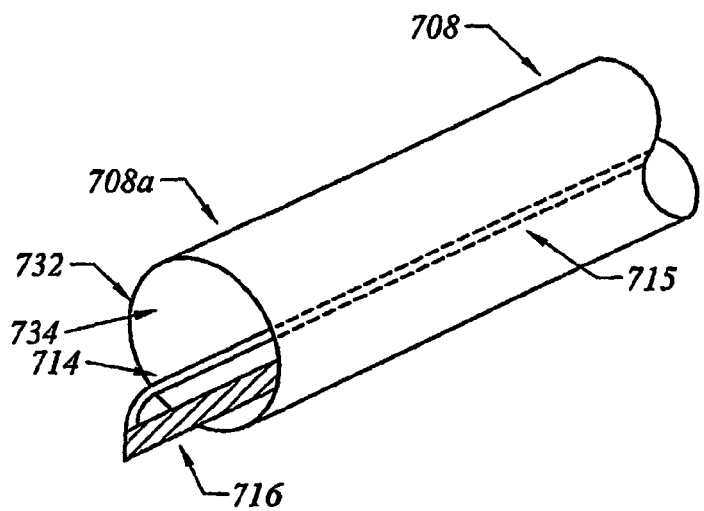
FIG. 7B is a perspective view of the distal end portion of the rotating member of FIG. 7A shown in isolation from the shaft, according to another embodiment of the invention.

With reference to FIGS. 7A-B, FIG. 7A is a perspective view of the distal end of an instrument 701, including an elongate shaft 702 and a rotating member 708 housed within shaft 702, according to another embodiment of the invention. FIG. 7B is a perspective view of the distal end portion of rotating member 708 of FIG. 7A shown in isolation from shaft 702.

With reference to FIG. 7A, an aperture formed in shaft distal end portion 702a defines a tissue removal port 750.

Instrument 701 further includes an electrode support 716 which extends distally from rotating member distal end 708a. Electrode support 716 typically comprises an electrically insulating material such as a ceramic, a glass, or a silicone rubber. An active electrode 714 is affixed to the distal end of electrode support 716. Instrument 701 is configured such that active electrode 714 traverses port 750 as rotating member 708 rotates within shaft 702.

As shown in FIGS. 7A-B, active electrode 714 comprises an arcuate conductive element which extends proximally from support 716 to rotating member 708. In particular, a first distal end of the arcuate conductive element is affixed to a distal end of electrode support 716, and a second end of the arcuate conductive element is affixed to rotating member 708, such that active electrode 714 spans a void between a distal portion of electrode support 716 and the distal end of rotating member 708. The arcuate conductive element may comprise a metal wire comprising a material such as stainless steel, molybdenum, platinum, tungsten, palladium, iridium, titanium, or their alloys, and the like. The arcuate conductive element (e.g., metal wire) may be circular or rectangular in cross-section, or may have various other cross-sectional shapes. Active electrode terminals having various cross-sectional shapes suitable for promoting high current density (high electric field intensity) are described in commonly assigned U.S. patent application Ser. No. 09/709,035, the disclosure of which is incorporated by reference herein in its entirety.

An active electrode lead 715, coupled to active electrode 714, extends proximally for connection of active electrode 714 to an electrosurgical generator or power supply. Alternative active electrode configurations are also possible under the invention.

Typically, instrument 701 includes a return electrode disposed at the working end of instrument 701. The return electrode is not shown in FIGS. 7A-B for the sake of clarity. Various return electrode configurations are possible (see, e.g., FIGS. 9A-C).

As shown, rotating member 708 is in the form of an open cylinder. In one embodiment, the longitudinal void within member 708 defines an aspiration lumen 734 extending distally to an aspiration port 732. Aspiration lumen 734 may be coupled proximally to a suitable vacuum source, as is well known in the art. Accordingly, resected tissue fragments, ablation by-products, and other unwanted materials may be removed from the surgical site via aspiration port 732 and aspiration lumen 734.

Figure 8A:
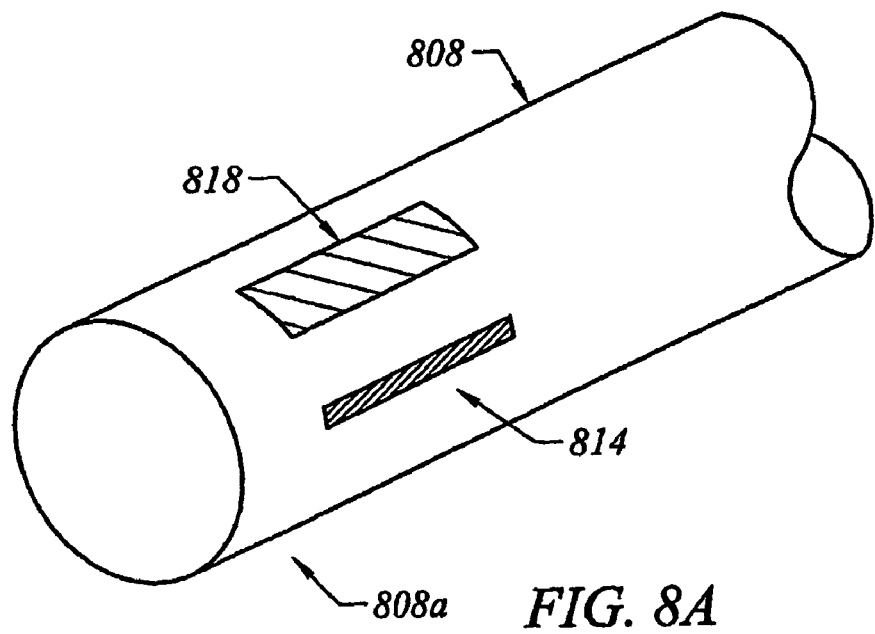
FIG. 8A is a perspective view of the distal end of a rotating member of an electrosurgical instrument.
Figure 8B:
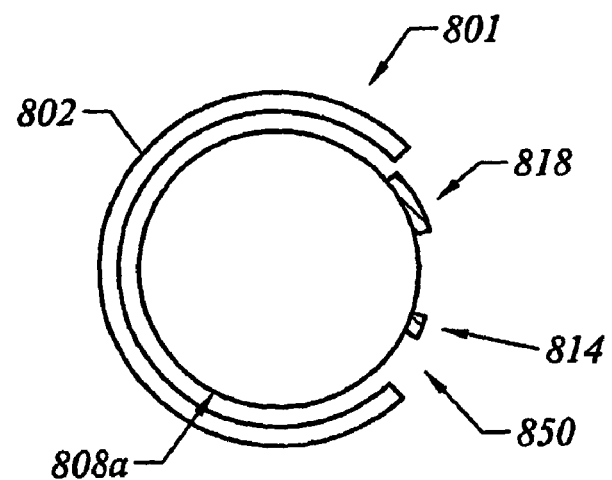
FIG. 8B is a transverse sectional view showing the distal end of the rotating member of FIG. 8A within a shaft of the instrument, according to another embodiment of the invention.

With reference to FIGS. 8A-B, FIG. 8A is a perspective view of the distal end of a rotating member 808 of an electrosurgical instrument 801, according to another embodiment of the invention. FIG. 8B is a transverse sectional view showing a distal end 808a of rotating member 808 disposed within a shaft 802 of instrument 801. Instrument 801 may have certain features analogous or similar to those of other embodiments of the invention as shown and described hereinabove. Thus, instrument 801 includes a tissue removal port 850 (FIG. 8B). Tissue removal port 850 may be in the form of a substantially circular or oval aperture arranged laterally on the distal end portion of shaft 802 (see, e.g., FIGS. 6A, 7A). Removal port may also be placed distally such that it forms part of the distal tip of the shaft 802.

Again with reference to FIGS. 8A-B, an active electrode 814 and a return electrode 818 are disposed on rotating member distal end 808a. Active electrode 814 and return electrode 818 are configured such that active electrode 814 and return electrode 818 sequentially traverse tissue removal port 850 as rotating member 808 rotates within shaft 802. During use of instrument 801, port 850 is positioned in at least close proximity to a target tissue. Upon application of a suitable high frequency voltage between active electrode 814 and return electrode 818, at least a portion of the target tissue is removed as rotating member 808 rotates within shaft 802. Typically, such tissue removal is effected via plasma induced molecular dissociation of target tissue components (e.g., Coblation®, described supra). Suitable voltage parameters for the ablation of tissue according to the invention are presented hereinabove. Active electrode 814 and return electrode 818 are represented in FIG. 8A as elongate strips. However, it is to be understood that other electrode geometries and configurations are also within the scope of the invention.

Figure 9A:
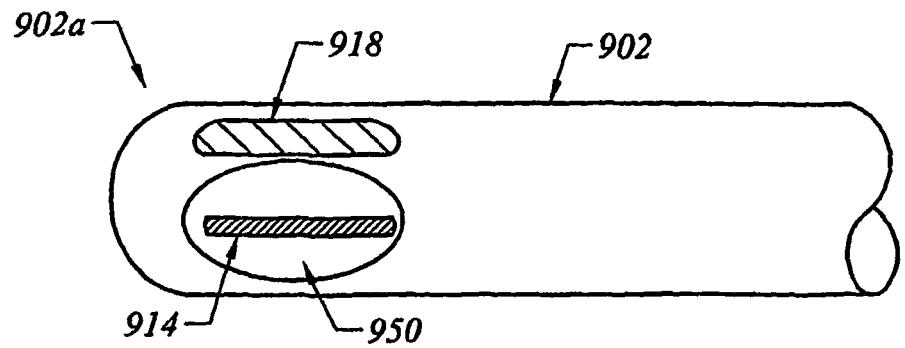
FIGS. 9A-C each schematically represent the working end of an electrosurgical instrument showing various return electrode configurations, according to three different embodiments of the invention.
Figure 9B:
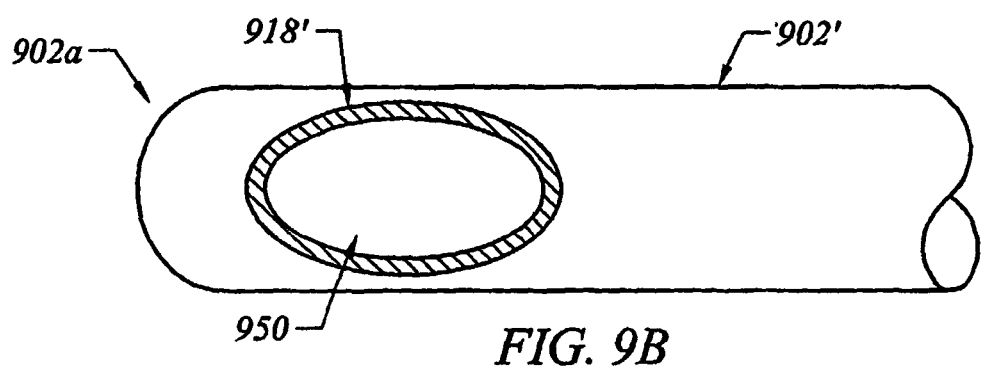
Figure 9C:
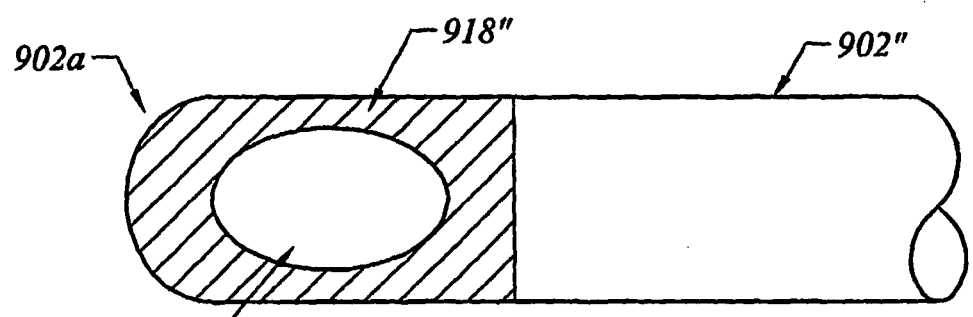

FIGS. 9A-C each schematically represent the working end of an electrosurgical instrument showing various return electrode configurations, according to three different embodiments of the invention. In each of FIGS. 9A-C, there is shown a shaft including a shaft distal end portion 902a having a tissue removal port 950 therein. An active electrode 914 is schematically represented in FIG. 9A as an elongate strip.

In the embodiment of FIG. 9A, an elongate return electrode 918 is disposed at shaft distal end portion 902a adjacent to tissue removal port 950. In the embodiment of FIG. 9B, a return electrode 918' surrounds tissue removal port 950 as an annulus of conductive material. Each of shafts 902 (FIG. 9A) and 902' (FIG. 9B) may comprise an electrically conductive material encased within an electrically insulating layer, and each of return electrodes 918 (FIG. 9A) and 918' (FIG. 9B) may comprise an exposed, non-insulated portion of shafts 902, 902', respectively. Alternatively, return electrodes 918 and 918' may be discrete electrodes having leads attached thereto for coupling to an electrosurgical generator. In the latter situation (discrete electrodes), return electrodes 918 and 918' may comprise a material such as stainless steel, molybdenum, platinum, tungsten, palladium, iridium, titanium, or their alloys, and the like.

In the embodiment of FIG. 9C, a return electrode 918" surrounds tissue removal port 950. Shaft 902" may comprise an electrically conductive material, such as stainless steel, having a proximal portion encased within a layer of electrically insulating material. An exposed, non-insulated, distal portion of shaft 902" defines return electrode 918". Other return electrode configurations are also within the scope of the invention.

Figure 10:
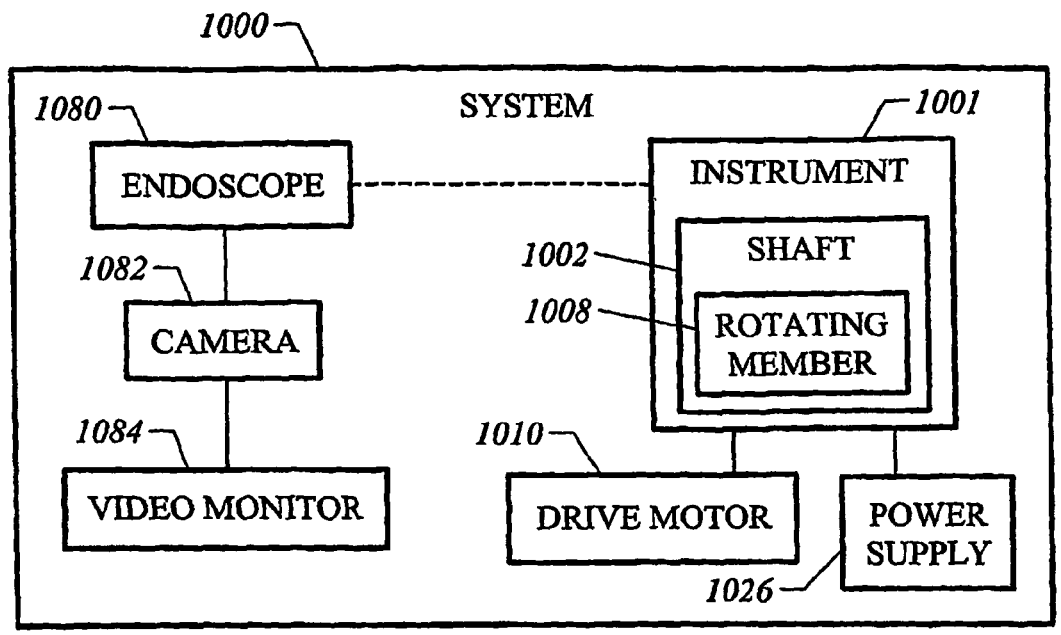
FIG. 10 is a block diagram schematically representing an endoscopic electrosurgical system, according to another embodiment of the invention.

In one embodiment, instruments of the invention are adapted for performing endoscopic procedures. For example, instruments of the invention may be adapted for performing arthroscopic procedures, e.g., on the ankle, knee, hip, wrist, elbow, or shoulder. FIG. 10 is a block diagram schematically representing an endoscopic electrosurgical system 1000. System 1000 typically includes an endoscope 1080; an instrument 1001, which may be adapted for use in conjunction with endoscope 1080; a power supply 1028 for supplying a high frequency voltage to instrument 1001; as well as a camera 1082 and a monitor 1084 adapted for viewing a working end of instrument 1001 and the surgical site.

Instrument 1001 typically comprises a bipolar electrosurgical probe having active and return electrodes (not shown in FIG. 10) disposed at the working end of instrument 1001. Instrument 1001 includes an outer shaft 1002, and a rotating member 1008 housed within shaft 1002. A tissue removal port (e.g., FIGS. 4-9C) is typically arranged laterally at a distal end portion of shaft 1002. The active and return electrodes may be disposed on shaft 1002, or on rotating member 1008, as described hereinabove for various embodiments of the invention (e.g., with reference to FIGS. 5A-B, 7A-B). System 1000 further includes a drive motor 1010 for driving the rotation of rotating member 1008 within shaft 1002. Drive motor 1010 is shown in FIG. 10 as a separate unit coupled to instrument 1001, although in alternative embodiments the drive motor may be integral with either the probe or the power supply, as described hereinabove.

Instrument 1001 is adapted for the controlled removal of target tissue from a surgical site during various endoscopic procedures. Typically, tissue removal is effected by the molecular dissociation of target tissue components during application of a high frequency voltage between the active and return electrodes. Instrument 1001 may also be adapted for coagulating severed blood vessels. In this regard, instrument may further include a dedicated coagulation electrode (e.g., FIG. 4) for effecting hemostasis during a procedure. Alternatively, one or both of the active and return electrodes may be adapted for coagulation and hemostasis.

Figure 11:
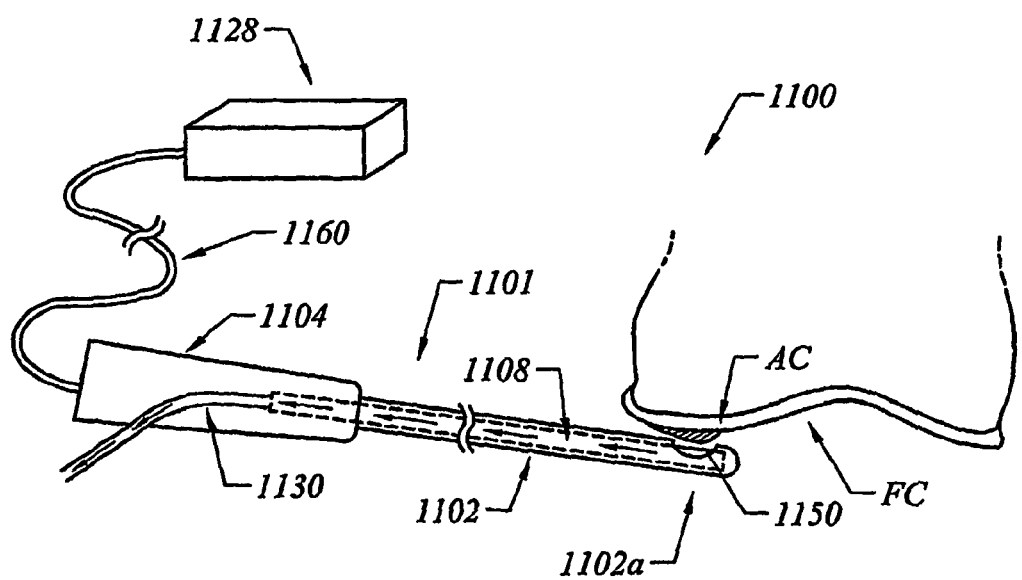
FIG. 11 schematically represents a surgical procedure performed using an instrument which incorporates a rotating member, according to another embodiment of the invention.

As a further example of the utility of the invention, the reader's attention is now drawn to FIG. 11, which schematically represents an arthroscopic procedure using an electrosurgical system 1100, according to one embodiment of the invention. Of course, it is to be understood that the invention is by no means limited to arthroscopic procedures. System 1100 includes an instrument 1101 coupled to an electrosurgical generator or power supply 1128 via a connector cable 1160. Instrument 1101 includes a shaft 1102 having a shaft distal end portion 1102a, and a tissue removal port 1150 at shaft distal end portion 1102a. Instrument 1101 further includes a rotating member 1108 configured to rotate within shaft 1102. Instrument 1101 further includes an aspiration element 1130 extending longitudinally within instrument 1101 from shaft distal end portion 1102a to a proximal handle 1104.

Instrument 1101 still further may include an active electrode and a return electrode (neither of which are shown in FIG. 11). As described hereinabove, according to one embodiment of the invention, the active electrode may be disposed on shaft 1102 and rotating member 1108 may be adapted to guide target tissue towards the active electrode as a portion of rotating member 1108 traverses tissue removal port 1150. Tissue entering the port's threshold will be separated from tissue outside the port's threshold. In an alternative embodiment, the active electrode may be disposed on rotating member 1108 such that the active electrode traverses tissue removal port 1150 as rotating member 1108 rotates within shaft 1102. Regardless of the electrode configuration, instrument 1101 is adapted for the controlled removal of target tissue, via molecular dissociation of target tissue components upon application of a high frequency voltage between the active and return electrodes, during rotation of rotating member 1108. Instruments of the invention are suited, inter alia, to the removal, or shaping, of relatively hard connective tissue, such as articular cartilage, meniscal cartilage, tendons, or ligaments of a synovial joint.

For illustrative purposes, FIG. 11 shows a femoral condyle, FC having a roughened or fibrous region of articular cartilage, AC, wherein the roughened or fibrous region of articular cartilage represents a target tissue to be removed, shaped, or sculpted to provide a smooth region of articular cartilage. According to a method of the invention, the distal end of shaft 1102 is positioned such that tissue removal port 1150 is in at least close proximity to the target tissue. In some embodiments, instrument 1101 is positioned such that tissue removal port 1150 contacts the target tissue. Also, tissue may be positioned within the port wherein tissue entering the port is separated from tissue outside the threshold.

While the instrument is suitably positioned with respect to the target tissue, rotating member 1108 is driven to rotate at a suitable speed within shaft 1102 by a drive motor (not shown in FIG. 11), as described hereinabove. While rotating member 1108 is being rotatively driven within shaft 1102, a high frequency voltage is applied between the active and return electrodes via power supply 1128. In this way, the target tissue is sequentially removed as the rotating member distal end traverses the tissue removal port. While the voltage is being applied between the electrodes and the rotating member is being rotatively driven, the tissue removal port may be translated with respect to the target tissue, e.g., to shape the tissue at the surgical site.

The removal of tissue using instrument 1101, via molecular dissociation of tissue components, typically results in resected tissue fragments as well as gaseous ablation by-products. Such tissue fragments and by-products, together with other excess or unwanted materials, may be removed from the surgical site via aspiration element 1130 in an aspiration stream (indicated by solid arrows in FIG. 11).

Power supply 1128 is typically switchable between the ablation mode (for tissue removal), and the sub-ablation mode (for coagulating blood vessels and inducing hemostasis). In this regard, instrument 1101 is further adapted for coagulation, and in some embodiments may have a dedicated coagulation electrode (e.g., FIG. 4). Power supply 1128 may be conveniently controlled, for example, switched between the ablation and sub-ablation modes, e.g. via one or more foot pedals. Accordingly, tissue removal (ablation) and coagulation of bleeding blood vessels (hemostasis) can be readily achieved using a single instrument.

As mentioned above, the active electrode may be positioned on the rotating member or on the outer tubular member. The active electrode is thus a certain distance (radial separation) from the central axis of the rotating member. In the present invention, this radial distance may be varied (e.g., reduced). Indeed, an active electrode may be disposed on a small-radii rotating member. Additionally, the active electrode may have a cone or other shape that varies (e.g., decreases) in radius with axial length. Still other variations of the present invention may be built in accordance with the disclosure hereinabove.

While the exemplary embodiments of the present invention have been described in detail, by way of example and for clarity of understanding, a variety of changes, adaptations, and modifications will be apparent to those of skill in the art. In addition, it is to be understood that certain elements or features of various disclosed embodiments may be substituted for corresponding or analogous elements or features of other disclosed embodiments, or may be combined with elements and features of other disclosed embodiments, without departing from the scope of the instant invention. Therefore, the scope of the present invention is limited solely by the appended claims.

What is claimed is:

1. An electrosurgical instrument for removing target tissue, comprising:
   a shaft including a shaft distal end portion and a shaft proximal end portion, the shaft having a longitudinal void therein;
   a tissue removal port disposed at the shaft distal end portion;
   an elongate rotating member comprising at least one leading edge and housed longitudinally within the longitudinal void of the shaft, the rotating member adapted to rotate within the shaft, the rotating member coupled to a drive motor for driving rotation of the rotating member;
   a discrete active electrode disposed on a first portion of the tissue removal port edge, the active electrode adapted to electrosurgically remove at least a portion of the target tissue via molecular dissociation of target tissue components as the rotating member leading edge manipulates tissue toward the active electrode;
an active electrode lead extending proximally from the active electrode and disposed internal to the shaft distal end portion; and
a return electrode disposed at the instrument distal end on a second portion of the tissue removal port edge.

2. The instrument of claim 1, further comprising an aspiration unit including an elongate aspiration lumen in communication distally with an aspiration port.

3. The instrument of claim 2, wherein the aspiration port is in fluid communication with the tissue removal port.

4. The instrument of claim 1, further comprising a coagulation electrode disposed at the instrument distal end.

5. The instrument of claim 1, wherein at least one of the active electrode and the return electrode is adapted for coagulating tissue or a blood vessel.

6. The instrument of claim 1, wherein the active electrode and the return electrode are elongate shapes arranged on diametrically opposite sides of the port.

7. The instrument of claim 1 wherein the active electrode has an elongate edge disposed along a portion of the port edge and wherein the return electrode has an elongate edge disposed along a second portion of the port edge and wherein the spacing between the active and return electrodes edges are approximately constant.

8. A method for the controlled removal of a target tissue at a surgical site, comprising:
a) providing an electrosurgical instrument, the instrument including a shaft having a shaft distal end portion, a tissue removal port disposed at the shaft distal end portion, an elongate rotating member housed longitudinally within the shaft, the rotating member having at least one leading edge and adapted to rotate within the shaft, a discrete active electrode disposed on at least a portion of the edge of the tissue removal port, an active electrode lead extending proximally from the active electrode and disposed internal to the shaft distal end portion, and a return electrode disposed at the instrument distal end on a second portion of the tissue removal port edge;
b) positioning the instrument distal end with respect to the target tissue such that the tissue removal port lies in at least close proximity to the target tissue;
c) driving the rotating member via a drive motor such that the rotating member rotates within the shaft and manipulates the target tissue toward the active electrode; and
d) during said step c), applying a high frequency voltage between the active electrode and the return electrode, wherein the active electrode is adapted for electrosurgically removing the target tissue via molecular dissociation of target tissue components as the rotating member rotates within the shaft such that the leading edge repeatedly manipulates the target tissue toward the active electrode.

9. The method of claim 8, wherein the said step b) comprises positioning the shaft distal end portion at or within a synovial joint of the patient.

10. The method of claim 8, wherein the target tissue comprises articular cartilage, meniscal cartilage, a ligament, or a tendon.

11. The method of claim 8, wherein the voltage applied in said step d) is in the range of from about 200 volts RMS to 1500 volts RMS.

12. The method of claim 8, wherein said step c) comprises driving the rotating member at a speed in the range of from about 20 rpm to 90 rpm.

13. The method of claim 8, further comprising:
e) during said steps c) and d), manipulating the instrument such that the tissue removal port is translated with respect to the target tissue.

14. The method of claim 8, wherein said steps c) and d) generate fragments of resected tissue and gaseous ablation by-products, and the method further comprises:
f) aspirating the fragments of resected tissue and gaseous ablation by-products via an aspiration unit, wherein the aspiration unit is integral with the instrument.

15. An electrosurgical instrument for removing target tissue from a patient, comprising:
a shaft including a shaft distal end portion and a shaft proximal end portion, the shaft having a longitudinal void therein and a tissue removal port disposed laterally on the shaft distal end portion and spaced proximally from the shaft distal end;
an active electrode disposed on a first portion of an edge of the tissue removal port;
a return electrode disposed on the shaft distal end portion and spaced from the active electrode, and wherein the return electrode is disposed on a second portion of the tissue removal port edge; and
a rotating member housed longitudinally within the longitudinal void of the shaft, the rotating member adapted to rotate within the shaft, the rotating member including a rotating member distal end, the rotating member distal end configured to traverse the tissue removal port as the rotating member rotates within the shaft, and the active electrode is adapted to remove the target tissue as the rotating member distal end traverses the tissue removal port.

16. The instrument of claim 15, wherein the active electrode is elongate in shape, and wherein the active electrode is oriented so that the elongate dimension is disposed on the port edge.

17. The instrument of claim 15, wherein the second portion of the edge is spaced from the first portion of the edge.

18. The instrument of claim 15, wherein the active electrode comprises a discrete electrode coupled to an active electrode lead, the active electrode lead extending proximally within the shaft, and the active electrode lead adapted for coupling the active electrode to an electrosurgical generator.

19. The instrument of claim 15, wherein at least a portion of the shaft is encased within an electrically insulating layer, and the active electrode comprises an exposed, non-insulated region of the shaft.

20. The instrument of claim 15, wherein the rotating member has a leading edge to manipulate the target tissue towards the active electrode as the rotating member leading edge traverses the tissue removal port.

21. The instrument of claim 20, wherein the active electrode is adapted to electrosurgically remove at least a portion of the target tissue via molecular dissociation of target tissue components as the target tissue is manipulated towards the active electrode.

22. The instrument of claim 15, wherein at least the leading edge of the rotating member is electrically non-conducting.

23. The instrument of claim 15, wherein the rotating member distal end is adapted to provide friction between the rotating member and the target tissue.

24. The instrument of claim 15, wherein the rotating member is coupled to a drive motor for driving rotation of the rotating member within the shaft at a speed in the range of from about 20 rpm to 90 rpm.

25. The instrument of claim 15, further comprising a coagulation electrode disposed at the distal tip of the shaft.

26. An electrosurgical system for treating a target tissue, comprising:
   an instrument which comprises:
   a shaft including a shaft distal end portion and a shaft proximal end portion, the shaft having a longitudinal void therein;
   a tissue removal port at the shaft distal end portion;
   an elongate rotating member housed within the shaft and adapted to rotate therein, the rotating member having a distal end configured to traverse the tissue removal port as the rotating member rotates within the shaft;
   an active electrode disposed on a first portion of an edge of the tissue removal port, the active electrode adapted to electrosurgically remove a portion of the target tissue during each revolution of the rotating member; and
   a return electrode disposed at the instrument distal end on a second portion of the tissue removal port edge; and
   an electrosurgical generator coupled to the instrument for applying a high frequency voltage between the active electrode and the return electrode, wherein the active electrode is adapted to electrosurgically remove at least a portion of the target tissue upon application of the high frequency voltage.

27. The system of claim 26, wherein the rotating member comprises a leading edge, the leading edge operable to manipulate the target tissue towards the active electrode as the rotating member leading edge traverses the tissue removal port.

28. The system of claim 26, further comprising a drive motor, wherein the rotating member is coupled to the drive motor via a flexible transmission line for driving rotation of the rotating member within the shaft.

29. The system of claim 28, wherein the drive motor is integral with the electrosurgical generator.

30. The system of claim 26, wherein the active electrode and the return electrode are both elongate shapes arranged on opposite sides of the port edge.

31. The system of claim 26, wherein at least a distal portion of the rotating member has an arcuate cross-sectional shape.

32. A method of removing a target tissue of a patient, comprising:
   a) providing an electrosurgical instrument, the instrument including a shaft having a shaft distal end portion, the shaft distal end portion having a tissue removal port therein, the instrument further including a rotating member adapted to rotate within the shaft, an active electrode disposed on a first portion of an edge of the tissue removal port, and a return electrode disposed on a second portion of the tissue removal port edge, the rotating member having a leading edge;
   b) positioning the shaft distal end portion in at least close proximity to the target tissue;
   c) rotatively driving the rotating member such that the rotating member leading edge repeatedly traverses the tissue removal port and thereby manipulates a portion of the target tissue toward the active electrode; and
   d) during said step c), applying a high frequency voltage between the active electrode and the return electrode, whereby tissue is sequentially removed upon application of the high frequency voltage between the active electrode and the return electrode and as the rotating member leading edge repeatedly traverses the tissue removal port.

33. The method of claim 32, wherein during said steps c) and d), the target tissue is removed via molecular dissociation of target tissue components.

34. The method of claim 32, wherein during said steps c) and d), the active electrode is adapted to remove the target tissue as the leading edge traverses the tissue removal port.

35. The method of claim 32, wherein said step c) comprises driving the rotating member at a speed in the range of from about 20 rpm to 90 rpm.

36. The method of claim 32, wherein the target tissue comprises articular cartilage, meniscal cartilage, a ligament, or a tendon.

37. The method of claim 32, wherein said step d) comprises applying a radio frequency alternating-current voltage in the range of from about 200 volts RMS to 1500 volts RMS.

* * * * *